United States Patent
Kokoris et al.

(10) Patent No.: US 10,774,105 B2
(45) Date of Patent: Sep. 15, 2020

(54) PHOSPHOROAMIDATE ESTERS, AND USE AND SYNTHESIS THEREOF

(71) Applicant: Stratos Genomics, Inc., Seattle, WA (US)

(72) Inventors: Mark Stamatios Kokoris, Bothell, WA (US); John Tabone, Kirkland, WA (US); Melud Nabavi, Seattle, WA (US); Aaron Jacobs, Seattle, WA (US)

(73) Assignee: STRATOS GENOMICS, INC., Seattle, WA (US)

( * ) Notice: Subject to any disclaimer, the term of this patent is extended or adjusted under 35 U.S.C. 154(b) by 0 days.

(21) Appl. No.: 16/380,882

(22) Filed: Apr. 10, 2019

(65) Prior Publication Data

US 2019/0330254 A1  Oct. 31, 2019

Related U.S. Application Data

(63) Continuation of application No. 14/947,540, filed on Nov. 20, 2015, now Pat. No. 10,301,345.

(60) Provisional application No. 62/082,488, filed on Nov. 20, 2014.

(51) Int. Cl.
| | |
|---|---|
| *C07H 19/10* | (2006.01) |
| *C07H 19/14* | (2006.01) |
| *C07F 9/6574* | (2006.01) |
| *C07H 23/00* | (2006.01) |

(52) U.S. Cl.
CPC ......... *C07H 19/10* (2013.01); *C07F 9/65746* (2013.01); *C07H 19/14* (2013.01); *C07H 23/00* (2013.01)

(58) Field of Classification Search
CPC ..... C07F 9/65746; C07H 19/14; C07H 19/10; C07H 23/00
See application file for complete search history.

(56) References Cited

U.S. PATENT DOCUMENTS

| | | | |
|---|---|---|---|
| 5,432,272 | A | 7/1995 | Benner |
| 6,150,510 | A | 11/2000 | Seela et al. |
| 7,939,259 | B2 | 5/2011 | Kokoris et al. |
| 8,324,360 | B2 | 12/2012 | Kokoris et al. |
| 8,586,301 | B2 | 11/2013 | Kokoris et al. |
| 8,592,182 | B2 | 11/2013 | Kokoris et al. |
| 9,670,526 | B2 * | 6/2017 | Kokoris ............... C12Q 1/6806 |
| 9,771,614 | B2 * | 9/2017 | Kokoris ............... C12P 19/34 |
| 10,301,345 | B2 * | 5/2019 | Kokoris ............... C07F 9/65746 |
| 2014/0134618 | A1 | 5/2014 | Kokoris et al. |
| 2015/0284787 | A1 | 10/2015 | Kokoris et al. |

FOREIGN PATENT DOCUMENTS

| | | |
|---|---|---|
| WO | 92/02258 A1 | 2/1992 |
| WO | 93/10820 A1 | 6/1993 |
| WO | 94/22892 A1 | 10/1994 |
| WO | 94/24144 A2 | 10/1994 |
| WO | 2008/052775 A2 | 5/2008 |
| WO | 2008/128686 A1 | 10/2008 |
| WO | 2008/157696 A2 | 12/2008 |
| WO | 2015/175789 A1 | 11/2015 |

OTHER PUBLICATIONS

Berner et al., "Studies on the role of tetrazole in the activation of phosphoramidites," *Nucleic Acids Research* 17(3):853-864, 1989.
Dahl et al., "Mechanistic studies on the phosphoramidite coupling reaction in oligonucleotide synthesis. I. Evidence for nucleophilic catalysis by tetrazole and rate variations with the phosphorus substituents," *Nucleic Acids Research* 15(4):1729-1743, 1987.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," *Tetrahedron* 54:3607-3630, 1998.
Koukhareva et al., "Synthesis and properties of NTP analogs with modified Triphosphate chains," *Nucleoside Triphosphates and their Analogs, Chemistry, Biotechnology, and Biological Applications*, Taylor & Francis, USA, pp. 39-104, Jan. 1, 2005.
Vargeese et al., "Efficient activation of nucleoside phosphoramidites with 4,5-dicyanoimidazole during oligonucleotide synthesis," *Nucleic Acids Research* 26(4):1046-1050, 1998.
Wolfe et al., "Synthesis and polymerase of 5'-amino-2',5'-dideoxy-5'-N-triphosphate nucleotides," *Nucleic Acids Research* 30(17):3739-3747, 2002.
Machacek et al., "Sequencing by Expansion: A Novel Technology Enabling Rapid Clinical DNA Sequencing", ASHG, Oct. 16-20, 2018.

\* cited by examiner

*Primary Examiner* — Lawrence E Crane
(74) *Attorney, Agent, or Firm* — Seed IP Law Group LLP

(57) ABSTRACT

Phosphoramidate esters and related nucleotide analogs useful in polynucleotide sequencing techniques, and synthetic methods for preparing those compounds, are disclosed, including compounds having the following structure:

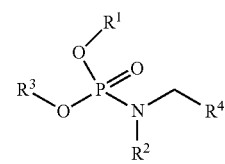

wherein $R^1$, $R^2$, $R^3$ and $R^4$ are as defined herein. These compounds include nucleotide phosphoramidates analogs that are modified on the alpha-phosphate to enable attachment of a variety of application-specific substituents such as tether molecules.

10 Claims, 1 Drawing Sheet

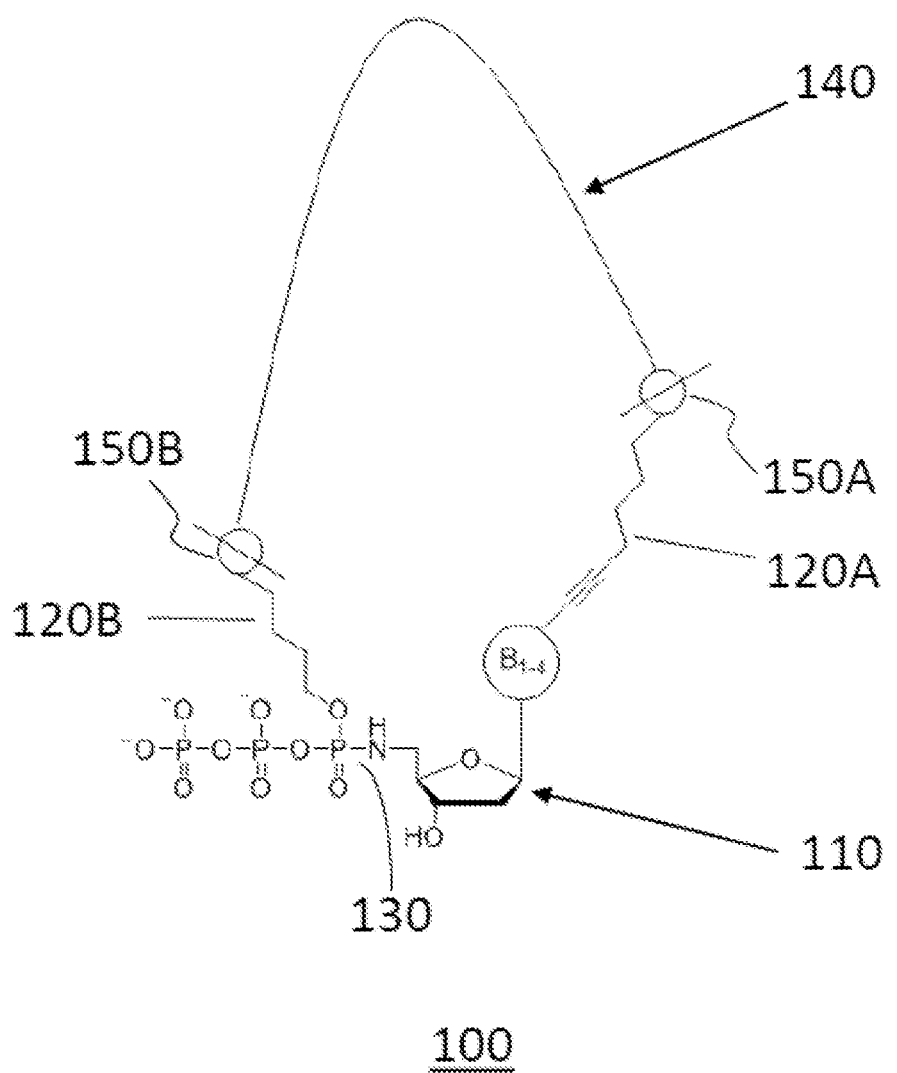

US 10,774,105 B2

PHOSPHOROAMIDATE ESTERS, AND USE AND SYNTHESIS THEREOF

CROSS-REFERENCE TO RELATED APPLICATIONS

This application is a continuation of U.S. application Ser. No. 14/947,540 filed Nov. 20, 2015 (now issued as U.S. Pat. No. 10,301,345), and claims the benefit under 35 U.S.C. § 119(e) of U.S. provisional application Ser. No. 62/082,488, filed Nov. 20, 2014, both of which are incorporated herein by reference in their entirety.

FIELD OF THE INVENTION

The present invention is in the field of phosphoroamidate ester compounds, synthetic methods for making said compounds, and methods for the determination of nucleic acids using said compounds, e.g., in the field of single molecule sequencing.

BACKGROUND

Chemically modified nucleotides have been extensively used in the study of many complicated biological systems. In particular, they have proven indispensable in the analysis of protein-nucleic acid interactions, the determination of genotypes, and the sequencing of nucleic acids. In general, these applications rely on differences in the chemical reactivity or electronic properties of the modified nucleotides as compared to the naturally occurring counterpart. Analogs of nucleotide triphosphates (NTPs) may be synthesized with modifications at the base, sugar, or triphosphate chain. Historically, modification of the triphosphate chain has been mainly used to study enzymatic pathways, which results in hydrolysis and transfer of the phosphate from NTP to another molecule. Modification of sugar and base has served a number of different purposes, from pharmaceutical to diagnostic applications.

In many examples of deoxyribonucleotide triphosphate (dNTP) analogs, the original $P^1$—O—$CH_2$(5') fragment has been modified. One common type of modification is the substitution of an oxygen atom with S, NH, or $CR^2$ (where R is H, an alkyl, or an aryl group and their derivatives). Interest in 5'-$NH_2$-dNTPs (i.e. 5' phosphoramidates and analogs), in particular, has increased due to their potential utility in genomic analysis (see, e.g., Shchepinov et al., Matrix-induced fragmentation of P3'-N5' phosphoramidate-containing DNA: high-throughput MALDI-TOF analysis of genomic sequence polymorphisms. Nuc. Acids Res. v. 30(17) pp. 3739-3747 (2002)) and DNA sequencing (see, e.g., U.S. Pat. No. 8,324,360 to Kokoris et al.). Certain useful features of 5' phosphoramidate analogs include their ability to exist in a triphosphate form, which can be utilized by many polymerases (see, e.g., Letsinger et al., Incorporation of 5'-amino-5'-deoxythymidine 5' phosphate in polynucleotides by use of DNA polymerase I and a phiX174 DNA template. Biochemistry v. 15 pp. 2810-2816 (1975)), and the ability to selectively cleave the P—N bond under acidic conditions (see, e.g., Letsinger et al., Enzymatic synthesis of polydeoxyribonucleotides possessing internucleotide phosphoramidate bonds. J. Am. Chem. Soc. v. 94 pp. 292-293 (1972)).

Modification of the dNTP alpha phosphate, in turn, has been exploited to introduce diverse functional properties, such as attachment points for detectable labels, solid state matrices, and other useful substituents. Examples of nucleotide analogs modified on the phosphate residue and various processes for producing such analogs have been described in several reviews. See, e.g., Koukhareva, Vaghefi and Lebedev, Nucleoside Triphosphates and their Analogs (2005) Chapter 2, "Synthesis and properties of NTP analogs with modified Triphosphate side chains", Ed. M. Vaghefi, CRC Press, Taylor & Francis, Boca Raton. Triphosphates are of particular importance as substrates for DNA or RNA polymerase that incorporate the nucleotide analogs into long chain nucleic acids. Generally, triphosphates are synthesized by first preparing the nucleoside monophosphates, which are subsequently converted into triphosphates enzymatically, for example, by kinases. However, nucleotide monophosphate (NMP) analogs may not be suitable substrates for kinase enzymes, and the preparation of such specific analogs thus will likely require unique chemical routes.

Though a variety of different analogs are available that mimic nucleotides and their polymers for diverse applications, there remains a need in the art for the development of novel analogs that offer unique combinations of individual properties while retaining the ability to be recognized and acted upon by enzymes. For example, the concept of "sequencing by expansion" has been described, in which a template nucleic acid is converted into an expandable daughter-strand polymeric "surrogate" through template-directed enzymatic synthesis. In one embodiment, the synthesis reaction incorporates dNTP analogs, referred to as "XNTPs" (see, e.g. Kokoris et al., U.S. Pat. No. 8,324,360). Once incorporated into the surrogate, cleavage of the selectively cleavable bonds can effectively expand the polymer, thus increasing the spatial resolution of the individual nucleotides. Such expanded nucleic acid molecules show great promise in, e.g., nanopore-based sequencing systems. For this particular application, it would be advantageous to provide improved polymerase substrate analogs that feature both a selectively cleavable bond and an attachment point for a bulky substituent, such that these features are introduced into the expandable surrogate daughter-strand product.

Thus, one technical object forming the basis of the present invention is to provide improved nucleotide phosphoramidate analogs that are further modified on the alpha-phosphate to enable attachment of a variety of application-specific substituents (e.g. tether molecules) and, furthermore, to provide reliable processes for the synthesis of such novel nucleotide analogs.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

BRIEF SUMMARY

Briefly stated, the present disclosure provides mono and polyphosphoroamidate ester compounds, synthetic methods for the preparation of such compounds, compounds useful in the synthetic methods, and uses for the compounds.

For example, in one aspect the present disclosure provides compounds of the formula (1)

(1)

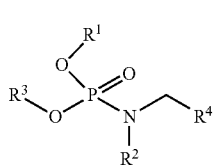

wherein, $R^1$ is selected from
a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and
b) an alkyl group and an oxyalkyl group, either of which terminates in a linker group (LG1), the LG1 bonded to a tether (T);

$R^2$ is selected from hydrogen and $C_1$-$C_4$alkyl;

$R^3$ is selected from $R^5$ and —[Pn-O]$_m$—$R^5$, where Pn is independently selected from P(OR$^5$) and P(=O)(OR$^5$) at each occurrence, and m is selected from 1, 2, 3, 4, 5 and 6;

$R^4$ is selected from

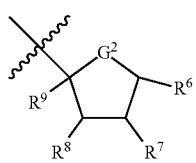 and 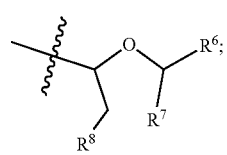

$R^5$ is selected from H and $G^1$;

$R^6$ is a heterocycle, the heterocycle optionally comprising a substituent $R^{13}$, where $R^{13}$ is selected from
a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and
b) an alkyl group and an oxyalkyl group, either of which terminates in a linker group (LG2), the LG2 bonded to the tether (T);

$R^7$ is selected from hydrogen, —CH$_2$-halogen, $C_1$-$C_4$alkyl, hydroxyl and —CH$_2$—OR$^{10}$;

$R^8$ is —OR$^{11}$ or —O-L-SS where L-SS represents a solid support optionally bound to a linker;

$R^9$ is hydrogen or, when $R^7$ is —CH$_2$—OR$^{10}$ then $R^9$ may be —CH$_2$—R$^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and CH$_2$; and $G^3$ is a protecting group for a hydroxyl group that is bonded to a carbon atom.

In another aspect, the present disclosure provides synthetic methods and compounds useful therein, for the preparation of mono and polyphosphoroamidate ester compounds. For example, the present disclosure provides a process for forming a phosphoromonoamidate diester 110 comprising contacting compound 100 with compound 105 to provide compound 110, the contacting conducted in the presence of a halide anion source,

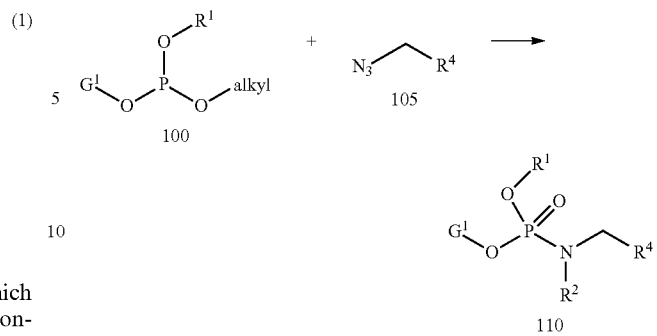

wherein:

$R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^2$ is selected from hydrogen and $C_1$-$C_4$alkyl;

$R^4$ is selected from

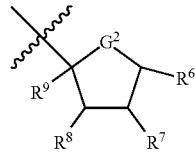 and 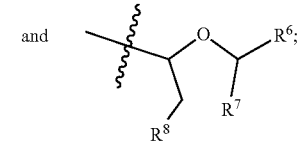

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —CH$_2$-halogen, $C_1$-$C_4$alkyl, hydroxyl and —CH$_2$—OR$^{10}$;

$R^8$ is —OR$^{11}$ or —O-L-SS where L-SS represents a solid support optionally bound to a linker;

$R^9$ is hydrogen or, when $R^7$ is —CH$_2$—OR$^{10}$ then $R^9$ may be —CH$_2$—R$^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and CH$_2$; and $G^3$ is a protecting group for a hydroxyl group that is bonded to a carbon atom.

As another example, the present disclosure provides a process of forming a phosphate protected N-phosphoroamidate-monoester diphosphate 120 comprising contacting a compound 110 with a compound 115 followed by oxidation to provide compound 120,

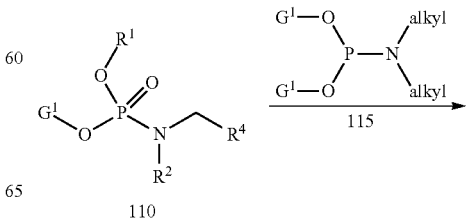

-continued

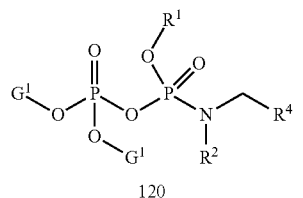
120 wherein:

$R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^2$ is selected from hydrogen and $C_1$-$C_4$alkyl;

$R^4$ is selected from

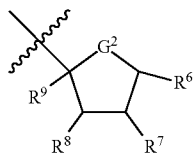 and 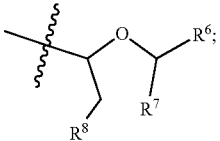

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and $CH_2$; and $G^3$ is a protecting group for a hydroxyl group that is bonded to a carbon atom.

As another example, the present disclosure provides a process of forming a phosphate protected N-phosphoroamidate-monoester triphosphate (125) comprising contacting a compound (120) with a compound (115) to provide, after oxidation, a phosphate protected N-phosphoroamidate-monoester triphosphate (125),

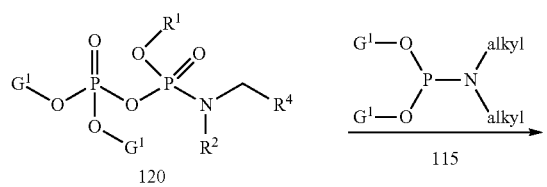

-continued

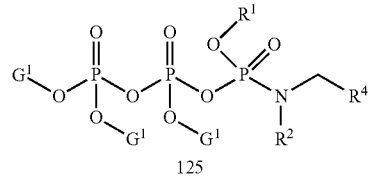
125 wherein:

$R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^2$ is selected from hydrogen and $C_1$-$C_4$alkyl;

$R^4$ is selected from

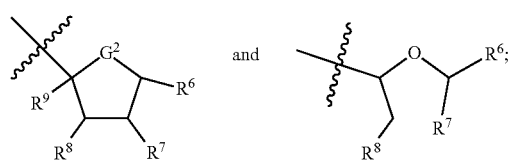

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and $CH_2$; and $G^3$ is a protecting group for a hydroxyl group that is bonded to a carbon atom.

As an example of a compound useful in the synthetic methods, in one embodiment the present disclosure provides a cyclic phosphite of the formula

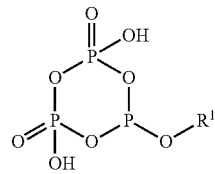

wherein $R^1$ is an alkyl group or an oxyalkyl group, either of which is terminally-functionalized, where the terminal functional group is selected from carbon-carbon double bond, carbon-carbon triple bond, hydroxyl, amine, azide, hydrazine, thiol, carboxyl or ester thereof, formyl, hydroxylamino and halogen. For example, in individual embodiments, the terminal functional group of $R^1$ may be carbon-carbon double bond; and/or it may be carbon-carbon triple bond; and/or it may be hydroxyl; and/or it may be amine; and/or it may be thiol; and/or it may be carboxyl or ester thereof; and/or it may be formyl; and/or it may be hydroxylamino; and/or it may be halogen. In one embodiment, $R^1$ comprises an alkyl group. For example, when $R^1$ is an alkyl group and the functional group is a carbon-carbon triple bond, $R^1$ may be $-(CH_2)_q-C\equiv CH$ where $-(CH_2)_q$ is the alkyl group, which might also be referred to as an alkylene group, and q is an integer selected from 2-10, e.g., $R^1$ is 1-hexynyl of the formula $-CH_2CH_2CH_2CH_2C\equiv CH$. In one embodiment, $R^1$ includes an electrophilic group. In one embodiment, $R^1$ includes a nucleophilic group. In one embodiment, $R^1$ includes a carboxylic acid or an ester thereof. In one embodiment, $R^1$ is an alkyl group which is terminally-functionalized. In one embodiment, $R^1$ is an oxyalkyl group which is terminally functionalized, where an oxyalkyl group may also be called an oxyalkylene group, and refers to an alkyl group that incorporates one or more oxygen atoms in the form of ether groups. Oxyethylene ($-O-CH_2-CH_2-$) groups and oxypropylene ($-O-CH_2-CH_2-CH_2-$) groups are exemplary oxyalkyl groups. The oxyalkyl group of $R^1$ may be formed from one or a plurality of oxyalkyl units, such as 2, 3, 4, 5, 6, 7, 8, 9, 10, or more than 10 repeating units.

In one embodiment of the present disclosure, the cyclic phosphite as described herein may be used in a process for forming a N-phosphoroamidate-monoester triphosphate (160) from the cyclotriphosphite (155) and an azide (105)

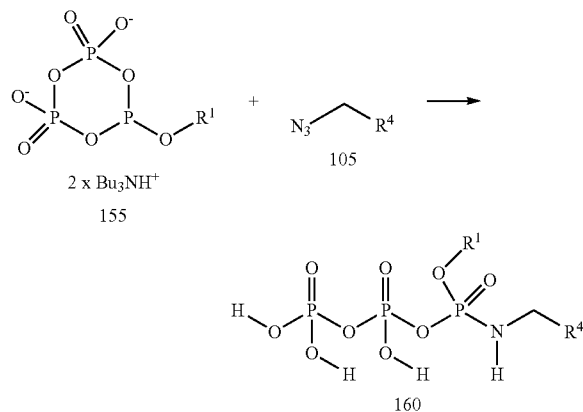

the process comprising combining (155) and (105) in the presence of suitable solvent and at a suitable temperature for a suitable reaction period, so as to form (160), wherein:

$R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^4$ is selected from

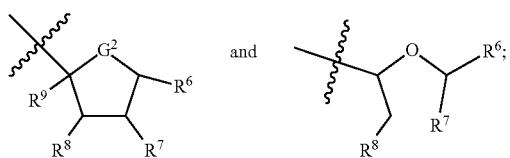

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, $-CH_2$-halogen, $C_1$-$C_4$alkyl, hydroxyl and $-CH_2-OR^{10}$;

$R^8$ is $-OR^{11}$ or $-O$-L-SS where L-SS represents a solid support optionally bound to a linker;

$R^9$ is hydrogen or, when $R^7$ is $-CH_2-OR^{10}$ then $R^9$ may be $-CH_2-R^{12}$ where $R^{10}$ and $R^{12}$ form a direct bond;

$R^{11}$ is selected from H and $G^3$;

$G^2$ is selected from oxygen, sulfur and $CH_2$; and $G^3$ is a protecting group for a hydroxyl group that is bonded to a carbon atom.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWING

The FIGURE illustrates how a nucleobase triphosphoramidate of the present disclosure may function as a component of a XNTP substrate useful in Sequencing by Expansion (SBX). In particular, the FIGURE illustrates a nucleobase triphosphoramidate (110) bearing one of the four standard nucleobases ($B_{1-4}$), wherein the nucleobase is linked to the triphosphoramidate via tether moiety (140), and cleavage of phosphoramidate bond (130) provides for linear expansion of the depicted compound. In the embodiment of the FIGURE, linkage of tether (140) to the nucleobase and triphosphoramidate is via conjugation sites (150A) and (150B), such as a triazole linkage, and such conjugation sites are, in turn, joined to the nucleobase ($B_{1-4}$) by linker group 120A and to the phosphoramidate by linker group 120B, which are shown as $C_6$ or $C_4$ hydrocarbon chains, respectively.

DETAILED DESCRIPTION OF THE INVENTION

The present invention is directed to one or more of new compounds, methods for preparing compounds including novel compounds useful in the synthetic methods, and the use of these compounds in, for example, nucleic acid sequencing techniques, each as disclosed herein. Prior to setting forth this disclosure in more detail, it may be helpful to an understanding thereof to provide definitions of certain terms to be used herein. Additional definitions are set forth throughout this disclosure.

"Independently at each occurrence" means that whenever a particular variable occurs, and that variable may be selected from two or more options, then at each occurrence of that variable, any of the two or more options may be selected, regardless of the selection made at any other occurrence of the variable. For example, when Pn is selected from —P(OR$^5$) and —P(═O)(OR$^5$) where m is selected from 2, 3, 4, 5 and 6, then at each of the 2-6 occurrences of Pn, Pn may represent —P(OR$^5$) or —P(═O)(OR$^5$), and R$^5$ is likewise independently selected at each occurrence. Unless otherwise specified, when a variable may be selected more than once in a formula, each selection is made independent at each occurrence of the variable.

Alkyl groups include straight chain and branched alkyl groups and cycloalkyl groups having from 1 to about 20 carbon atoms ($C_1$-$C_{20}$ alkyl or $C_{1-20}$ alkyl), and typically from 1 to 12 carbons ($C_1$-$C_{12}$ alkyl or $C_{1-12}$ alkyl) or, in some embodiments, from 1 to 8 carbon atoms ($C_1$-$C_8$ alkyl or $C_{1-8}$ alkyl) or, in some embodiments, from 1 to 4 carbon atoms ($C_1$-$C_4$ alkyl or $C_{1-4}$ alkyl) or, in some embodiments, from 1 to 3 carbon atoms ($C_1$-$C_3$ alkyl or $C_{1-3}$ alkyl). Examples of straight chain alkyl groups include, but are not limited to, methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. The alkyl group may be substituted or otherwise functionalized with a functional group. Representative substituted alkyl groups can be substituted one or more times with any non-alkyl group, for example, amino, hydroxy, cyano, carboxy, nitro, thio, alkoxy, and halogen groups. The alkyl group may contain one or more carbon-carbon double bonds and one or more carbon-carbon triple bonds along its structure. The term "terminally functionalized alkyl group" and its equivalent term "omega-functionalized alkyl group" refers to an alkyl group that terminates in a functional group. For example, the group —$CH_2CH_2CH_2CH_2$—OH represents a terminally functionalized n-butyl group having hydroxyl as the functional group, where this group may also be described as n-hydroxy $C_4$ alkyl.

Unsubstituted alkyl groups, which are optionally functionalized by the presence of carbon-carbon double bonds and/or carbon-carbon triple bonds, are examples of hydrocarbon groups, i.e., groups formed entirely of carbon and hydrogen. In one embodiment, the hydrocarbon group is an alkyl group. A $C_6$-$C_{16}$ hydrocarbon has 6, 7, 8, 9, 10, 11, 12, 13, 14, 15 or 16 carbon atoms in addition to hydrogen atoms as the only atoms present in the hydrocarbon moiety. As disclosed elsewhere herein, each of R$^1$ and R$^{13}$ may be a hydrocarbon alkyl group. As also disclosed elsewhere herein, each of R$^1$ and R$^{13}$ may be an oxyalkyl group.

Oxyalkyl refers to alkyl groups that are separated by oxygen, i.e., alkyl-O-alkyl- etc. and the like. Exemplary alkyl groups in an oxyalkyl unit are ethyl and propyl. Using ethyl as an example, oxyalkyl may refer to one or more repeating units of —$CH_2$—$CH_2$—O—. Thus, -ethyl-O-ethyl-O-ethyl-O-ethyl is an exemplary oxyalkyl group (where divalent ethyl is also referred to as ethylene). The number of repeating alkyl-O units (wherein divalent alkyl is referred to as alkylene) in an oxyalkyl may be, for example, 2, 3, 4, 5, 6, 7, 8, 9, 10, or more than 10.

Halogen refers to bromide, chloride, iodide and fluoride.

In the structures shown herein, when not all natural valencies of an atom are filled by named groups, it should be understood that the unfilled valencies are filled by hydrogen.

For example, the structure drawn as

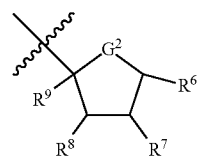

is equivalently drawn as

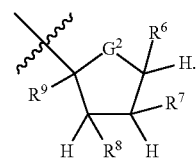

When a wavy line ⌇ in a chemical moiety intersects a bond, then the intersected bond is the location where the chemical moiety joins to the remainder of the molecule. All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

Heterocycle and heterocyclyl groups include aromatic and non-aromatic ring compounds (heterocyclic rings) containing 3 or more ring members, of which one or more is a heteroatom such as, but not limited to, N, O, S, or P. In some embodiments, heterocyclyl groups include 3 to 20 ring members, whereas other such groups have 3 to 15 ring members. At least one ring contains a heteroatom, but every ring in a heteropolycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-membered ring with two carbon atoms and three heteroatoms, a 6-membered ring with two carbon atoms and four heteroatoms and so forth. Likewise a $C_4$-heterocyclyl can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms.

The phrases "heterocycle" and "heterocyclyl group" includes fused ring species including those having fused aromatic and non-aromatic groups. The phrase also includes polycyclic ring systems containing a heteroatom and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, iso quinolinyl, tetrahydroquinolinyl, quinoxalinyl, and quinazolinyl groups.

As mentioned above, heterocyclyl groups may be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to substituted alkyl where the substituent may be, for example, halo, amino, hydroxy, cyano, carboxy, azide, (also referred to as an azido substituent), hydrazine (also referred to as a hydrazino subsitutent), nitro, thio, or alkoxy; unsaturated alkyl having, for example, carbon-carbon double bonds and/or carbon-carbon triple bonds; and alkyl groups that are both unsaturated and substituted.

Heteroaryl groups are aromatic ring compounds containing 5 or more ring members, of which, one or more is a heteroatom such as, but not limited to, N, O, and S. A heteroaryl group designated as a $C_2$-heteroaryl can be a 5-membered ring with two carbon atoms and three heteroatoms, a 6-membered ring with two carbon atoms and four heteroatoms and so forth. Likewise a $C_4$-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, iso quinolinyl, tetrahydroquinolinyl, tetrahydroisoquinolinyl, quinoxalinyl, and quinazolinyl groups.

The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with substituents such as those listed herein.

In one embodiment, the heterocycle group is a "nucleobase", where this term refers to a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-$N^6$-methyladenine, 2-aminoadenine, 7-deazaxanthine, 7-deazaguanine, 7-deaza-adenine, $N^4$-ethanocytosine, 2,6-diaminopurine, $N^6$-ethano-2,6diaminopurine, 5-methylcytosine, -5-($C_3$-$C_6$)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and published PCT applications WO 92/002258, WO 93/10820, WO 94/22892 and WO 94/24144, and Fasman ("Practical Handbook of Biochemistry and Molecular Biology", pp. 385-394, 1989, CRC Press, Boca Raton, La.), all herein incorporated by reference in their entireties. In one embodiment, the nucleobase is selected from adenine, guanine, uridine, and cytosine, and analogs of these nucleobases, such as those analogs disclosed herein.

"Nucleobase residue" includes nucleotides, nucleosides, fragments thereof, and related molecules having the property of binding to a complementary nucleotide. Deoxynucleotides and ribonucleotides, and their various analogs, are contemplated within the scope of this definition. Nucleobase residues may be members of oligomers and probes. "Nucleobase" and "nucleobase residue" may be used interchangeably herein and are generally synonymous unless context dictates otherwise.

In one embodiment, the heterocycle may be denoted by the symbol "$B_{1-4}$", wherein the subscript indicates that the heterocycle may be any one of the four standard nucleobases, A, C, G, or T, or an analog thereof wherein one atom of a natural base is replaced with a different atom which typically allows for additional substitution on the nucleobase.

In one embodiment, the heterocycle is a heterocyclic base. Heterocyclic bases are well known in the art as being nitrogen containing ring structures bound though a glycosidic bond to a sugar moiety, such as a pentose (e.g., D-ribose and 2-deoxy-D-ribose), where the sugar moiety may be bonded to a phosphate, such as a monophosphate, a diphosphate and a triphosphate. Exemplary heterocyclic bases are purines and pyrimidines. Exemplary purines ae adenine and guanine, while exemplary pyrimidines are cytosine, uracil and thymine. The heterocyclic base includes substituted heterocyclic bases and analogs of a naturally occurring heterocyclic base wherein a native atom is replaced with a different atom (e.g., a nitrogen normally found in a heterocyclic base may be replaced with carbon, e.g., C—H or C-substituent). See, e.g., Nucleic acids in chemistry and biology. Edited by C. Michael Blackburn and Michael J. Gait, Oxford and New York: Oxford University Press, 1996, pp. xix+ 528.

$G^1$ is H or a protecting group for a hydroxyl group that is bonded to a phosphorous atom. In one embodiment, $G^1$ is a protecting group for a hydroxyl group that is bonded to a phosphorous atom, or in other words, $G^1$ is a protecting group that is bonded to an oxygen, where the oxygen is bonded to a phosphorous, so that the protecting group is protecting what would otherwise be a hydroxyl group bonded to the phosphorous atom. $G^3$ is a protecting group for a hydroxyl group that is bonded to a carbon. In other words, $G^3$ is a protecting group that is bonded to an oxygen, where the oxygen is bonded to a carbon atoms, so that the protecting group is protecting what would otherwise be a hydroxyl group bonded to a carbon atom. Protecting groups can render chemical functionality inert to specific reaction conditions and can be appended to and removed from such functionality in a molecule without substantially damaging the remainder of the molecule. Practitioners in the art would be familiar with suitable protecting groups for use in the synthetic methods of the invention. See, e.g., Greene and Wuts, Protective Groups in Organic Synthesis, 2" ed., John Wiley k Sons, New York, 1991 and Peter G. M. Wuts, "Greene's Protective Groups in Organic Synthesis: Fifth Edition", Wiley, 2014.

When a term refers to an integer selected from a range, then that term may be any integer within that range, including the ends of the range. For example, when q is an integer selected from 2-10, then q can be any of 2, 3, 4, 5, 6, 7, 8, 9 and 10.

SS represents a solid support such as controlled pore glass (CPG). SS-L represents a solid support that is optionally bonded to a linking group, unless the presence of the linking groups is specifically excluded. Unless otherwise specified, a linking group is optionally inserted between a solid support and the compound being synthesized by solid phase chemistry as disclosed herein.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

In one embodiment, the present disclosure provides a compound of the formula (1)

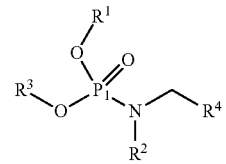

wherein,
$R^1$ is selected from
a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and
b) an alkyl group and an oxyalkyl group, either of which terminates in a linker group (LG1), the LG1 bonded to a tether (T);
$R^2$ is selected from hydrogen and $C_1$-$C_4$alkyl;
$R^3$ is selected from $R^5$ and —[Pn-O]$_m$—$R^5$, where Pn is independently selected from —P(OR$^5$) and —P(=O)(OR$^5$) at each occurrence, and m is selected from 1, 2, 3, 4, 5 and 6;
$R^4$ is selected from

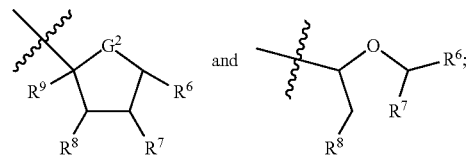

$R^5$ is selected from H and $G^1$;
$R^6$ is a heterocycle, optionally substituted with $R^{13}$, where $R^{13}$ is selected from
a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and
b) an alkyl group and an oxyalkyl group, either of which terminates in a linker group (LG2), the LG2 bonded to the tether (T);
$R^7$ is selected from hydrogen, —CH$_2$-halogen, $C_1$-$C_4$alkyl, hydroxyl and —CH$_2$—OR$^{10}$;
$R^8$ is —OR$^{11}$ or —O-L-SS where L-SS represents a solid support optionally bound to a linker;
$R^9$ is hydrogen or, when $R^7$ is —CH$_2$—OR$^{10}$ then $R^9$ may be —CH$_2$—R$^{12}$ where $R^{10}$ and $R^{12}$ form a direct bond;
$R^{11}$ is selected from H and $G^3$;
$G^1$ is H or a protecting group for a hydroxyl group that is bonded to a phosphorous atom;
$G^2$ is selected from oxygen, sulfur and CH$_2$; and
$G^3$ is a protecting group for a hydroxyl group that is bonded to a carbon atom.

Unless otherwise specified, the following descriptions of $R^1$, $R^2$, etc. may be used to further describe any of the compounds and synthetic methods disclosed herein which are described in terms of $R^1$, $R^2$, etc.

In one embodiment, the $R^1$ group is a terminally-functionalized alkyl group, where the functional group is selected from, for example, carbon-carbon double bond, carbon-carbon triple bond, nucleophilic groups such as hydroxyl, thiol or amino, electrophilic groups such as halogen, or other reactive groups such as carboxyl, formyl (aldehyde) and hydroxyamino. In optional embodiments: the functional group is carbon-carbon double bond; the functional group is carbon-carbon triple bond; the functional group is hydroxyl; the functional group is amine; the functional group is thiol; the functional group is halogen; the functional group is carboxyl or an ester thereof; the functional group is formyl, also known as aldehyde (—C(═O)H); the functional group is hydroxylamine. In optional embodiments, the alkyl group is a straight chain or a branched alkyl group having from 1 to about 20 carbon atoms ($C_1$-$C_{20}$ alkyl or $C_{1-20}$ alkyl), or 1 to 12 carbons ($C_1$-$C_{12}$ alkyl or $C_{1-12}$ alkyl) or 1 to 8 carbon atoms ($C_1$-$C_8$ alkyl or $C_{1-8}$ alkyl) or 1 to 4 carbon atoms ($C_1$-$C_4$ alkyl or $C_{1-4}$ alkyl) or, in some embodiments, from 1 to 3 carbon atoms ($C_1$-$C_3$ alkyl or $C_{1-3}$ alkyl). In one embodiment, $R^1$ is a hydrocarbon group such as —$(CH_2)_q$—C≡CH and q is an integer selected from 2-10, e.g., $R^1$ may be 1-hexynyl of the formula —$CH_2CH_2CH_2CH_2$C≡CH. In one embodiment, $R^1$ includes an electrophilic group as part of its structure, preferably the electrophilic group being at the terminus of the $R^1$ group. In one embodiment, $R^1$ includes a nucleophilic group as part of its structure, preferably the nucleophilic group being at the terminus of the $R^1$ group. In one embodiment, $R^1$ includes a carboxylic acid or an ester thereof as part of its structure, where the carboxylic acid or an ester thereof is preferably at the terminus of the $R^1$ group.

In another embodiment, $R^1$ is an oxyalkyl group which is terminally functionalized, where an oxyalkyl group may also be called an oxyalkylene group, and refers to an alkyl group that incorporates one or more oxygen atoms in the form of ether groups. For example, the oxyalkyl group may be an oxyethyl (—O—$CH_2$—$CH_2$—) group or an oxypropyl (—O—$CH_2$—$CH_2$—$CH_2$—) group, those being are exemplary oxyalkyl groups. The oxyalkyl group of $R^1$ may be formed from one or a plurality of oxyalkyl units, such as 2, 3, 4, 5, 6, 7, 8, 9, 10, or more than 10 repeating units. The functional group is selected from, for example, carbon-carbon double bond, carbon-carbon triple bond, nucleophilic groups such as hydroxyl, thiol or amino, electrophilic groups such as halogen, or other reactive groups such as carboxyl, formyl (aldehyde) and hydroxyamino. In optional embodiments: the functional group is carbon-carbon double bond; the functional group is carbon-carbon triple bond; the functional group is hydroxyl; the functional group is amine; the functional group is thiol; the functional group is halogen; the functional group is carboxyl or an ester thereof; the functional group is formyl, also known as aldehyde (—C(═O)H); the functional group is hydroxylamine. In optional embodiments, the alkyl portion of the oxyalkyl is a straight chain or a branched alkyl group having from 1 to about 20 carbon atoms ($C_1$-$C_{20}$ alkyl or $C_{1-20}$ alkyl), or 1 to 12 carbons ($C_1$-$C_{12}$ alkyl or $C_{1-12}$ alkyl) or 1 to 8 carbon atoms ($C_1$-$C_8$ alkyl or $C_{1-8}$ alkyl) or 1 to 4 carbon atoms ($C_1$-$C_4$ alkyl or $C_{1-4}$ alkyl) or, in some embodiments, has 1, 2 or 3 carbon atoms ($C_1$-$C_3$ alkyl or $C_{1-3}$ alkyl), or has 2 carbon atoms. In one embodiment, $R^1$ includes an electrophilic group as part of its structure, preferably the electrophilic group being at the terminus of the regroup. In one embodiment, $R^1$ includes a nucleophilic group as part of its structure, preferably the nucleophilic group being at the terminus of the regroup. In one embodiment, $R^1$ includes a carboxylic acid or an ester thereof as part of its structure, where the carboxylic acid or an ester thereof is preferably at the terminus of the regroup.

Thus, $R^1$ may be an alkyl group or an oxyalkyl group, either of which is terminally-functionalized, where the terminal functional group is selected from carbon-carbon double bond, carbon-carbon triple bond, hydroxyl, amine, azide, hydrazine, thiol, carboxyl or ester thereof, formyl, hydroxylamino and halogen.

The $R^2$ group is selected from hydrogen and $C_1$-$C_4$alkyl. In one embodiment, $R^2$ is hydrogen in each of the embodiments and embodiment combinations as disclosed herein. In another embodiment, $R^2$ is $C_1$, i.e., methyl.

The $R^3$ group is selected from $R^5$ and —$[Pn-O]_m$—$R^5$, where the term Pn is used to refer to the two options —P(OR$^5$) and —P(═O)(OR$^5$), where these two options are independently selected at each occurrence of Pn, and m is selected from 1, 2, 3, 4, 5 and 6. $R^5$ is selected from H and $G^1$; and $G^1$ is H or a protecting group for a hydroxyl group that is bonded to a phosphorous atom. In one embodiment, $R^3$ represents $R^5$, and $R^5$ is H. In another embodiment, $R^3$ represents $R^5$, and $R^5$ is a protecting group $G^1$.

In other embodiments, $R^3$ is —$[Pn-O]_m$—$R^5$. Thus, depending on the selections for —$[Pn-O]_m$—$R^5$, the present disclosure provides each of the following exemplary structures (1A)-(1K):

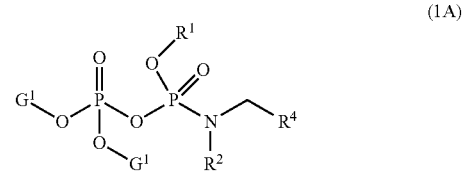
(1A)

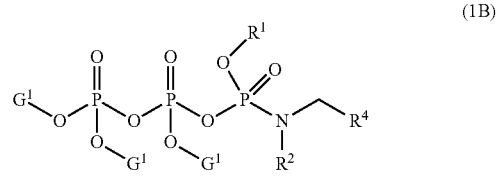
(1B)

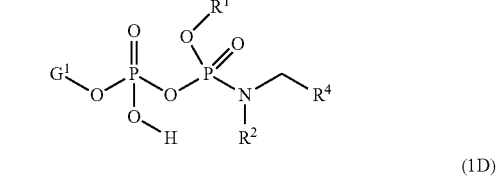
(1C)

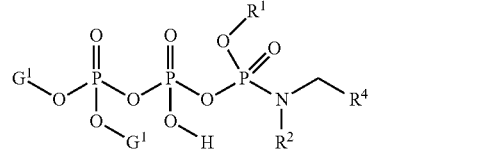
(1D)

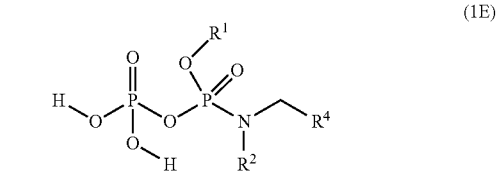
(1E)

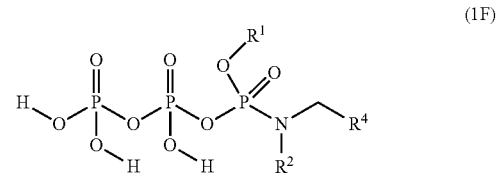
(1F)

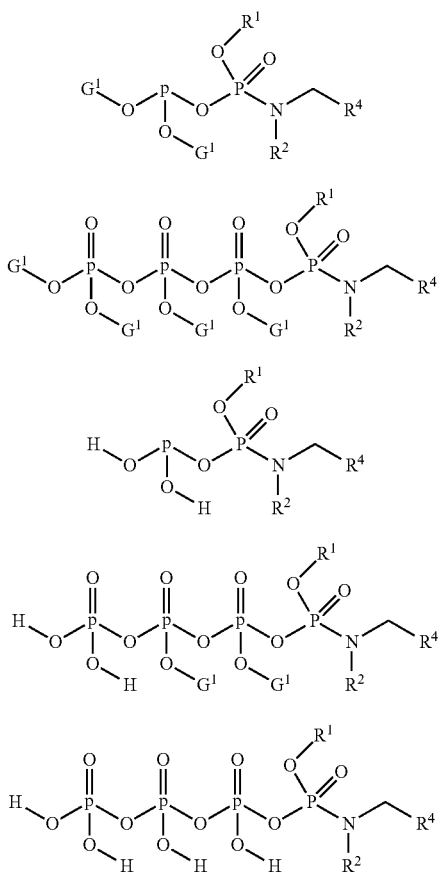

(1G)
(1H)
(1I)
(1J)
(1K)

Thus, the compounds of the present disclosure may have, for example, multiple phosphate groups or phosphate ester groups. In one embodiment, each of the phosphorous atoms is in the +5 valence state except for the terminal phosphorous atom which is in the +3 valence state, and $R^5$ may be hydrogen or $G^1$, independently selected at each occurrence. A few exemplary structures of this type are shown below as structures (1L)-(1Q):

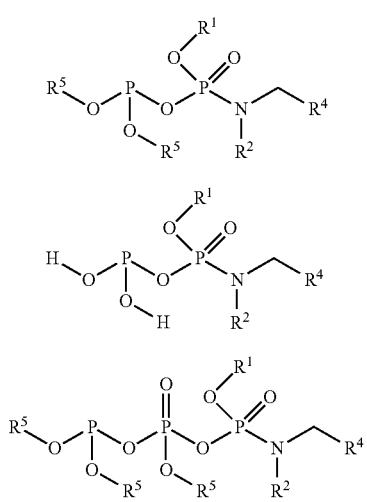

(1L)
(1M)
(1N)

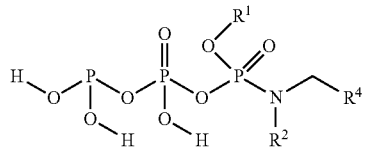

(1O)
(1P)
(1Q)

The $R^4$ group is selected from

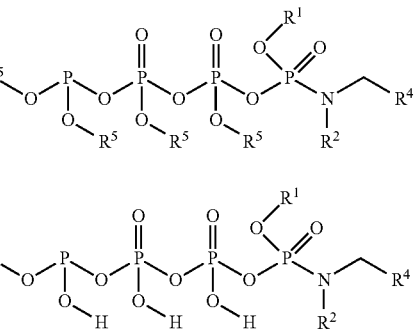

and

In one embodiment, $R^4$ is a cyclic group of the formula

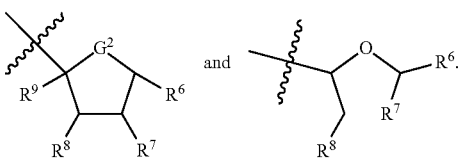

In another embodiment, the $R^4$ group is an acyclic groups of the formula

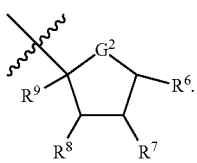

In either of these embodiments, $R^6$ is a heterocycle, where in optional embodiments $R^6$ is a nucleobase or a heterocyclic base that may be substituted with $R^{13}$ as defined herein.

Exemplary $R^6$ nucleobases are the $B_{1-4}$ nucleobases, where this term refers to a nucleobase selected from an adenosine analog, a guanosine analog, a uridine analog and a cytidine analog. For example, $B_{1-4}$ may refer to an adenosine analog of formula a guanosine analog of formula

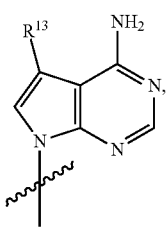

a uridine analog of formula

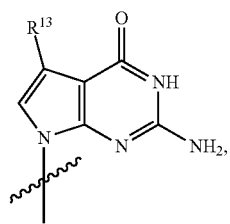

or a cytidine analog of formula

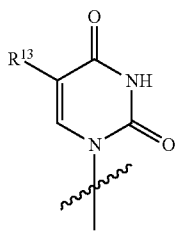

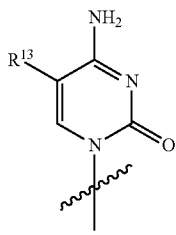

wherein $R^{13}$ is selected from an alkyl group and an oxyalkyl group, either of which is terminally functionalized. The term "either of which" as used herein refers to the alkyl group and the oxyalkyl group. Exemplary functional groups are selected from carbon-carbon double bond, carbon-carbon triple bond, hydroxyl, amine, azide, hydrazine, thiol, carboxyl, formyl, hydroxylamino and halogen. In one embodiment, the terminal functional group of $R^{13}$ and the terminal functional group of $R^1$ are the same functional group, for example, the terminal functional group of both $R^1$ and $R^{13}$ is a carbon-carbon triple bond such as shown in compound (11) disclosed elsewhere herein.

Thus, the $R^{13}$ group may be a terminally-functionalized alkyl group, where the functional group may be selected from carbon-carbon double bond, carbon-carbon triple bond, nucleophilic groups such as hydroxyl, thiol or amino, electrophilic groups such as halogen, or other reactive groups such as carboxyl, formyl (aldehyde) and hydroxyamino. In optional embodiments: the functional group is carbon-carbon double bond; the functional group is carbon-carbon triple bond; the functional group is hydroxyl; the functional group is amine; the functional group is thiol; the functional group is halogen; the functional group is carboxyl or an ester thereof; the functional group is formyl, also known as aldehyde (—C(═O)H); the functional group is hydroxylamine. In optional embodiments, the alkyl group is a straight chain or a branched alkyl group having from 1 to about 20 carbon atoms ($C_1$-$C_{20}$ alkyl or $C_{1-20}$ alkyl), or 1 to 12 carbons ($C_1$-$C_{12}$ alkyl or $C_{1-12}$ alkyl) or 1 to 8 carbon atoms ($C_1$-$C_8$ alkyl or $C_{1-8}$ alkyl) or 1 to 4 carbon atoms ($C_1$-$C_4$ alkyl or $C_{1-4}$ alkyl) or, in some embodiments, from 1 to 3 carbon atoms ($C_1$-$C_3$ alkyl or $C_{1-3}$ alkyl). In one embodiment, $R^1$ is a hydrocarbon alkyl group that is or includes the moiety —(CH$_2$)$_r$—C≡CH and r is an integer selected from 2-10, e.g., $R^{13}$ is or comprises 1-hexynyl of the formula —CH$_2$CH$_2$CH$_2$CH$_2$C≡CH. In one embodiment, $R^{13}$ includes an electrophilic group as part of its structure, preferably the electrophilic group being at the terminus of the $R^{13}$ group. In one embodiment, $R^{13}$ includes a nucleophilic group as part of its structure, preferably the nucleophilic group being at the terminus of the $R^{13}$ group. In one embodiment, $R^{13}$ includes a carboxylic acid or an ester thereof as part of its structure, where the carboxylic acid or an ester thereof is preferably at the terminus of the $R^{13}$ group. As mentioned elsewhere herein, in one embodiment the terminal reactive group of $R^1$ is identical to the terminal reactive group of $R^{13}$, e.g., both $R^1$ and $R^{13}$ terminate in a carbon-carbon triple bond, e.g., each may terminate in a —CH$_2$—CH$_2$—CH$_2$—CH$_2$—C≡CH group. In one embodiment, $R^{13}$ is or comprises an omega-functionalized $C_6$-$C_{16}$ hydrocarbon or an omega-functionalized $C_6$-$C_{16}$alkyl.

However, in another embodiment, the $R^{13}$ group may be a terminally-functionalized oxyalkyl group, where the functional group may be selected from carbon-carbon double bond, carbon-carbon triple bond, nucleophilic groups such as hydroxyl, thiol or amino, electrophilic groups such as halogen, or other reactive groups such as carboxyl, formyl (aldehyde) and hydroxyamino. In optional embodiments: the functional group is carbon-carbon double bond; the functional group is carbon-carbon triple bond; the functional group is hydroxyl; the functional group is amine; the functional group is thiol; the functional group is halogen; the functional group is carboxyl or an ester thereof; the functional group is formyl, also known as aldehyde (—C(═O)H); the functional group is hydroxylamine. In optional embodiments, the oxyalkyl group incorporates a straight chain or a branched alkyl group having from 1 to about 20 carbon atoms ($C_1$-$C_{20}$ alkyl or $C_{1-20}$ alkyl), or 1 to 12 carbons ($C_1$-$C_{12}$ alkyl or $C_{1-12}$ alkyl) or 1 to 8 carbon atoms ($C_1$-$C_8$ alkyl or $C_{1-8}$ alkyl) or 1 to 4 carbon atoms ($C_1$-$C_4$ alkyl or $C_{1-4}$ alkyl) or, in some embodiments, from 1 to 3 carbon atoms ($C_1$-$C_3$ alkyl or $C_{1-3}$ alkyl), while in one embodiment the alkyl group of each oxyalkyl unit has 2 carbons, and in another embodiment the alkyl group of each oxyalkyl unit has 3 carbons. In one embodiment, $R^{13}$ includes an electrophilic group as part of its structure, preferably the electrophilic group being at the terminus of the $R^{13}$ group. In one embodiment, $R^{13}$ includes a nucleophilic group as part of its structure, preferably the nucleophilic group being at the terminus of the $R^{13}$ group. In one embodiment, $R^{13}$ includes a carboxylic acid or an ester thereof as part of its structure, where the carboxylic acid or an ester thereof is preferably at the terminus of the $R^{13}$ group. As mentioned elsewhere herein, in one embodiment the terminal reactive group of $R^1$ is identical to the terminal reactive group of $R^{13}$, e.g., both $R^1$ and $R^{13}$ terminate in a carbon-carbon triple bond.

In one embodiment, $R^4$ is a heterocycle or nucleobase which includes $R^{13}$ as part of its structure, where $R^{13}$ is selected from omega-functionalized $C_6$-$C_{16}$ hydrocarbons or omega-functionalized $C_6$-$C_{16}$ alkyls. An exemplary $R^{13}$ group is —C≡C—(CH$_2$)$_4$—C≡CH in which case the omega functional group is a carbon-carbon triple bond.

Thus, in another embodiment, $R^4$ is a heterocycle or nucleobase which includes $R^{13}$ as a substituent, where $R^{13}$ is an alkyl group having a terminal carbon-carbon triple bond, and $R^1$ is an alkyl group having a terminal carbon-carbon triple bond, so that the compound of formula (1) may be a bis-alkyne deoxynucleoside polyphosphoramidate, e.g., a bis-alkyne deoxynucleoside triphosphoramidate. Such a bis-alkyne structure is a particularly useful compound to react with a tether precursor having terminal azide groups, i.e., $N_3$-tether-$N_3$, where the product of such a reaction comprises triazole groups that link the two ends of the tether (via LG1 and LG2, each of LG1 and LG2 being a triazole group) to a deoxynucleoside polyphosphoramidate such as a deoxynucleoside triphosphoramidate.

In one embodiment, $R^{13}$ is selected from omega-functionalized $C_6$-$C_{16}$ hydrocarbons or omega-functionalized $C_6$-$C_{16}$ alkyls. An exemplary $R^{13}$ group is —C≡C—(CH$_2$)$_4$—C≡CH in which case the omega functional group is a carbon-carbon triple bond.

The $R^7$ group is selected from hydrogen, —CH$_2$-halogen, $C_1$-$C_4$alkyl, hydroxyl and —CH$_2$—Or$^{10}$. In various embodiments: $R^7$ hydrogen; $R^7$ is —CH$_2$-halogen; $R^7$ is $C_1$-$C_4$alkyl; $R_7$ is hydroxyl and/or $R^7$ is —CH$^2$—OR$^{10}$. In one embodiment, $R^7$ is selected from hydrogen, —CH$_2$-halogen, $C_1$-$C_4$alkyl and —CH$_2$—OR$^{10}$.

The $R^8$ group is —OR$^{11}$ or —O-SSL. SSL and SS-L designate a solid support (SS) that is optionally bound to a linking (also referred to as a linker) group (L), where the linker group joins the solid support through an oxygen atom as shown, to the remainder of the molecule.

The $R^9$ group is hydrogen or, when $R^7$ is —CH$_2$—OR$^{10}$ then $R^9$ may be —CH$_2$—R$^{12}$ where $R^{10}$ and $R^{12}$ form a direct bond. In one embodiment, $R^9$ is hydrogen. In one embodiment, $R^7$ is —CH$_2$—OR$^{10}$ and $R^9$ is —CH$_2$—R$^{12}$ where $R^{10}$ and $R^{12}$ form a direct bond.

The $R^{11}$ group is H or a protecting group $G^3$; where $G^3$ is a protecting group for a hydroxyl group that is bonded to a carbon atom. In one embodiment, $R^{11}$ is hydrogen. In another embodiment, $R^{11}$ is a protecting group, $G^3$.

The $G^2$ group is selected from oxygen, sulfur and CH$_2$. In one embodiment, $G^2$ is oxygen. In one embodiment, $G^2$ is sulfur. In one embodiment, $G^2$ is CH$_2$.

In one embodiment, the present disclosure provides a compound of the formula (1)

wherein $R^1$, $R^2$, $R^3$ and $R^4$ are defined herein, and embodiments for $R^1$, $R^2$, $R^3$ and $R^4$ are provided, including embodiments for $R^5$, $R^6$, $R^7$, $R^8$, $R^9$, $R^{10}$, $R^{11}$, $R^{12}$ and $R^{13}$, $G^1$, $G^2$, $G^3$, Pn, m, d and r. In describing compound of formula (I), any two, or any three, or any four, or any five, or more than five of these various embodiments may be combined.

For example, in one embodiment the present disclosure provides a compound of the formula (2a)

(2a)

wherein $R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^2$ is selected from hydrogen and $C_1$-$C_4$alkyl;

$R^5$ is selected from H and $G^1$;

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —CH$_2$-halogen, $C_1$-$C_4$alkyl, hydroxyl and —CH$_2$—OR$^{10}$;

$R^8$ is —OR$^{11}$ or —O-L-SS where L-SS represents a solid support optionally bound to a linker;

$R^9$ is hydrogen or, when $R^7$ is —CH$_2$—OR$^{10}$ then $R^9$ may be —CH$_2$—R$^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and CH$_2$; and $G^3$ is a protecting group for a hydroxyl group that is bonded to a carbon atom.

In optional embodiments of compounds of formula (2a), $R^2$ is hydrogen; and independently $G^2$ is oxygen. For example, the present disclosure provides a compound of formula (2b)

(2b)

wherein $R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^5$ is selected from H and $G^1$;

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom; and $G^3$ is a protecting group for a hydroxyl group that is bonded to a carbon atom.

In another optional embodiment of compounds of formula (2a), $R^9$ is hydrogen. In addition, $G^2$ is oxygen and/or $R^2$ is hydrogen. For example, the present disclosure provides a compound of formula (2c)

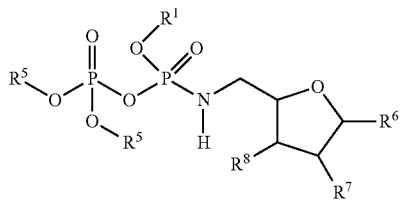

(2c)

wherein $R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^5$ is selected from H and $G^1$;

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker;

$R^{11}$ is selected from H and $G^3$;

$G^1$ is H or a protecting group for a hydroxyl group that is bonded to a phosphorous atom; and $G^3$ is a protecting group for a hydroxyl group that is bonded to a carbon atom.

The present disclosure also provides compounds corresponding to formulae (2a), (2b) and (2c) however the pentavalent phosphorous atom is trivalent. In other words, the present disclosure provides compounds of formula (2d), (2e) and (2f) where groups $R^1$, etc. are as defined above.

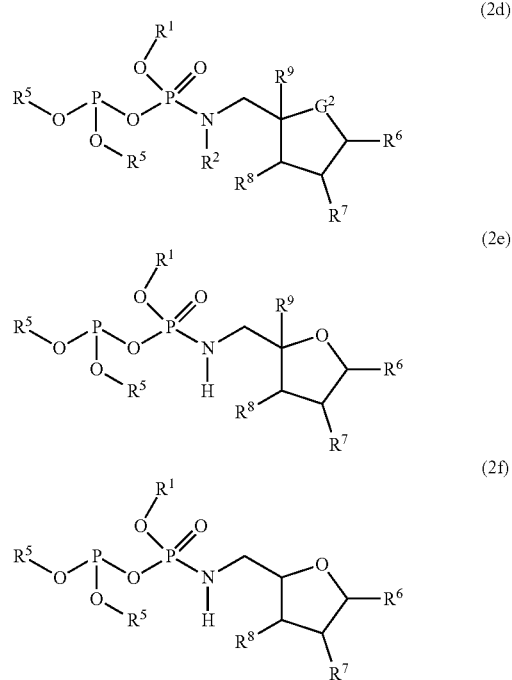

In specific embodiments of each of the compounds of formula (2a), (2b), (2c), (2d), (2e) and (2f): $R^1$ is a terminally-functionalized alkyl group, where the functional group is carbon-carbon triple bond, e.g., $R^1$ is —$(CH_2)_q$—C≡C and q is an integer selected from 2-10; and/or $R^5$ in at least one occurrence is hydrogen, and/or $R^5$ in at least one occurrence is $G^1$; and/or $R^6$ is a nucleobase or $R^6$ is a heterocyclic base; and/or $R^7$ is hydrogen; and/or $R^8$ is OH or $R^8$ comprises a solid support.

For example, in one embodiment the present disclosure provides a compound of the formula (3a)

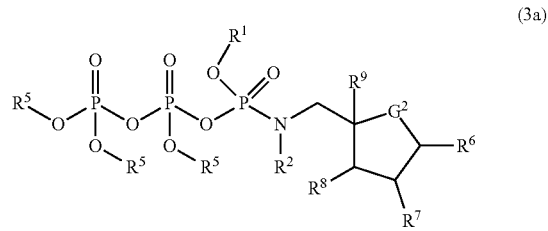

(3a)

wherein $R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^2$ is selected from hydrogen and $C_1$-$C_4$alkyl;

$R^5$ is selected from H and $G^1$;

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl and —$CH_2$—$OR^{10}$;

$R^8$ is —$OR^{11}$ or —O-L-SS where L-SS represents a solid support optionally bound to a linker;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and $CH_2$; and $G^3$ is a protecting group for a hydroxyl group that is bonded to a carbon atom.

In optional embodiments of compounds of formula (3a), $R^2$ is hydrogen; and independently $G^2$ is oxygen. For example, the present disclosure provides compound of formula (3b)

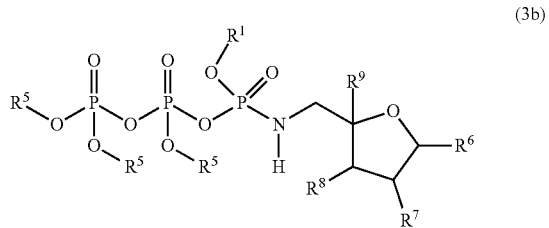

(3b)

wherein $R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^5$ is selected from H and $G^1$;

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom; and $G^3$ is a protecting group for a hydroxyl group that is bonded to a carbon atom.

In another optional embodiment of compounds of formula (3a), $R^9$ is hydrogen. In addition, $G^2$ is oxygen and/or $R^2$ is hydrogen. For example, the present disclosure provides a compound of formula (3c)

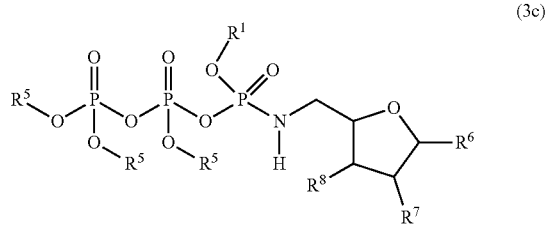

(3c)

wherein $R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^5$ is selected from H and $G^1$;

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, hydroxyl and $C_1$-$C_4$alkyl;

$R^8$ is —$OR^{11}$ or —O-L-SS where L-SS represents a solid support optionally bound to a linker;

$R^{11}$ is selected from H and $G^3$;

$G^1$ is H or a protecting group for a hydroxyl group that is bonded to a phosphorous atom; and $G^3$ is a protecting group for a hydroxyl group that is bonded to a carbon atom.

The present disclosure also provides compounds corresponding to formulae (3a), (3b) and (3c) however some of the pentavalent phosphorous atoms are trivalent. For example, the present disclosure provides compounds of formula (3d), (3e) and (3f) where groups $R^1$, etc. are as defined above.

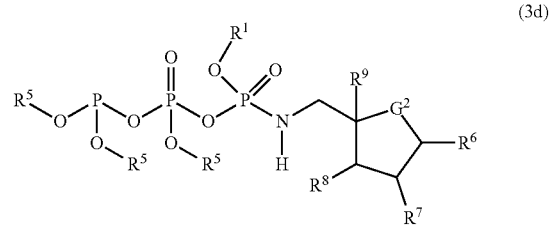

(3d)

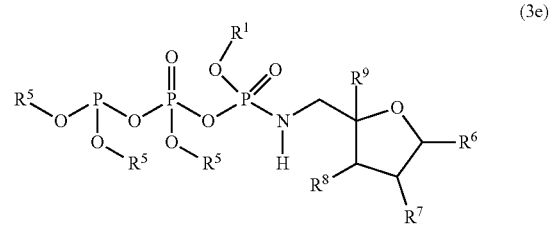

(3e)

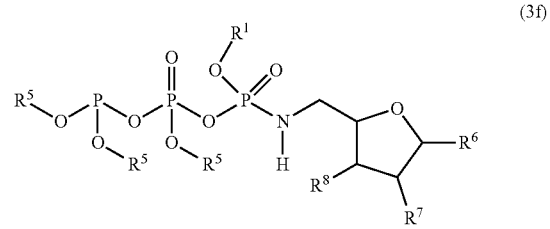

(3f)

In specific embodiments of each of the compounds of formula (3a), (3b), (3c), (3d), (3e) and (3f): $R^1$ is a terminally-functionalized alkyl group, where the functional group is carbon-carbon triple bond, e.g., $R^1$ is —$(CH_2)_q$—C≡C and q is an integer selected from 2-10; and/or $G^2$ is oxygen; and/or $R^5$ in at least one occurrence is hydrogen, and/or $R^5$ in at least one occurrence is $G^1$; and/or $R^6$ is a nucleobase or $R^6$ is a heterocyclic base; and/or $R^7$ is hydrogen; and/or $R^8$ is OH or $R^8$ comprises a solid support.

As another example, in one embodiment the present disclosure provides a compound of the formula (4a)

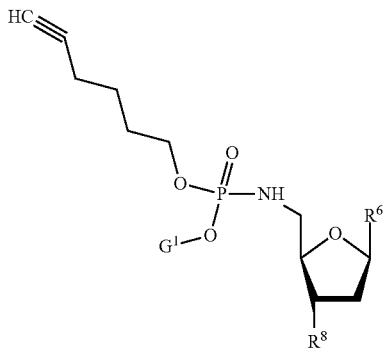

(4a)

wherein: G$^1$ is H or a protecting group; R$^6$ is a heterocycle; R$^8$ is selected from OR$^{11}$ and O—SS; R$^{11}$ is selected from H and G$^3$; G$^3$ is a protecting group for a hydroxyl group that is bonded to a carbon atom; and SS represents a solid support optionally bound to the O of O—SS via a linking group (L). In one embodiment, R$^8$ is hydroxyl. In one embodiment, R$^6$ is a nucleobase. In one embodiment, R$^6$ is a heterocyclic base. Optionally, the protecting group G$^1$ may be a 2-cyanoethyl group, giving rise to a compound of the present disclosure having the formula (4b)

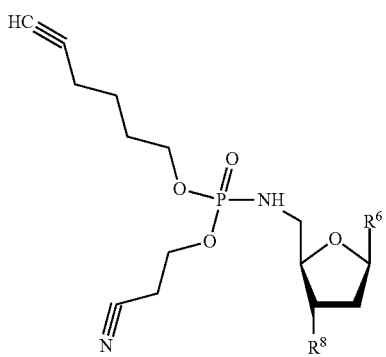

(4b)

wherein: R$^6$ is a heterocycle; R$^8$ is —OR$^{11}$ or —O-L-SS where L-SS represents a solid support optionally bound to a linker; R$^{11}$ is selected from H and G$^3$; G$^3$ is a protecting group for a hydroxyl group that is bonded to a carbon atom; and SS represents a solid support optionally bound to the O of O—SS via a linking group (L). In one embodiment, R$^8$ is hydroxyl. In one embodiment, R$^8$ is protected hydroxyl. In yet another embodiment, R$^8$ includes a solid support.

Optionally, R$^6$ is a nucleobase. For example, in one embodiment R$^6$ is a uridine analog. An exemplary uridine analog is shown in the compound of the formula (4c),

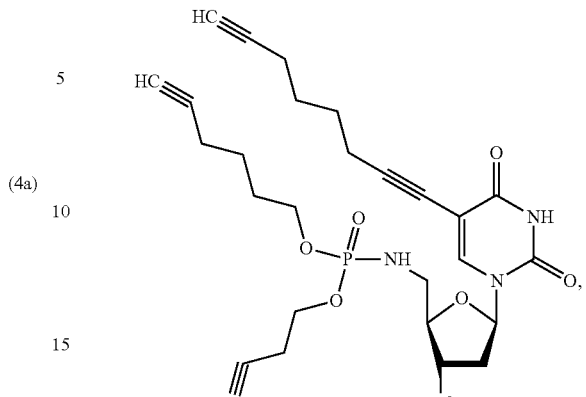

(4c)

wherein: G$^1$ is shown as cyanoethyl however other protecting groups may be substituted for cyanoethyl; R$^{13}$ is shown as —C≡C—(CH$_2$)$_4$—C≡CH however other omega-functionalized C$_6$-C$_{16}$ hydrocarbon groups may be substituted for —C≡C—(CH$_2$)$_4$—C≡CH; R$^8$ is —OR$^{11}$ or —O-L-SS where L-SS represents a solid support optionally bound to a linker; R$^{11}$ is selected from H and G$^3$; G$^3$ is a protecting group for a hydroxyl group that is bonded to a carbon atom; and SS represents a solid support optionally bound to the O of O—SS via a linking group. In one embodiment, R$^8$ is hydroxyl. In one embodiment, R$^8$ is protected hydroxyl. In yet another embodiment, R$^8$ includes a solid support. As another example, in one embodiment R$^6$ is a cytidine analog. An exemplary cytidine analog is shown in the compound of the formula (4d),

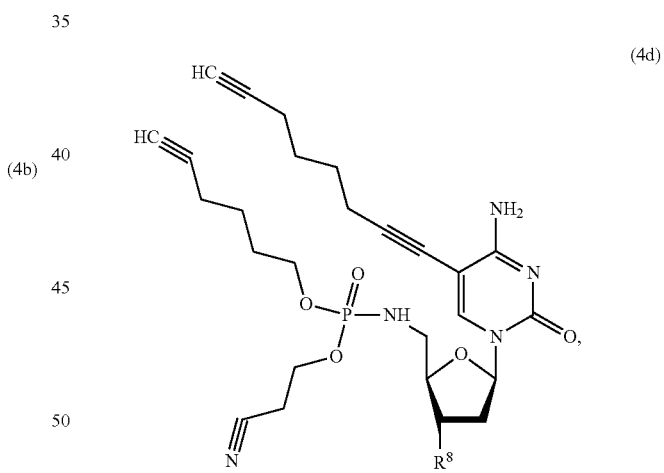

(4d)

wherein: G$^1$ is shown as cyanoethyl however other protecting groups may be substituted for cyanoethyl; R$^{13}$ is shown as —C≡C—(CH$_2$)$_4$—C≡CH however other omega-functionalized C$_6$-C$_{16}$ hydrocarbon groups may be substituted for —C≡C—(CH$_2$)$_4$—C≡CH; R$^8$ is —OR$^{11}$ or —O-L-SS where L-SS represents a solid support optionally bound to a linker; R$^{11}$ is selected from H and G$^3$; and G$^3$ is a protecting group for a hydroxyl group that is bonded to a carbon atom. In one embodiment, R$^8$ is hydroxyl. In one embodiment, R$^8$ is protected hydroxyl. In yet another embodiment, R$^8$ includes a solid support. As another example, in one embodiment R$^6$ is an adenosine analog. An exemplary adenosine analog is shown in the compound of the formula (4e),

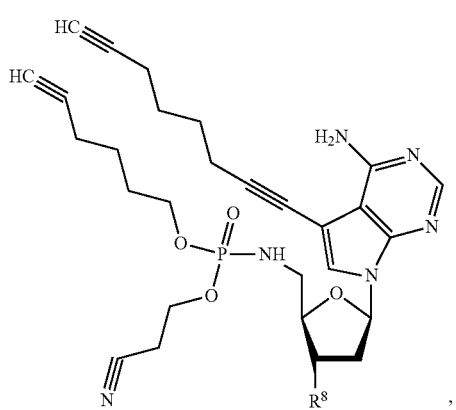

(4e)

wherein: G¹ is shown as cyanoethyl however other protecting groups may be substituted for cyanoethyl; R¹³ is shown as —C≡C—(CH$_2$)$_4$—C≡CH however other omega-functionalized C$_6$-C$_{16}$ hydrocarbon groups may be substituted for —C≡C—(CH$_2$)$_4$—C≡CH; R⁸ is —OR¹¹ or —O-L-SS where L-SS represents a solid support optionally bound to a linker; R¹¹ is selected from H and G³; and G³ is a protecting group for a hydroxyl group that is bonded to a carbon atom. In one embodiment, R⁸ is hydroxyl. In one embodiment, R⁸ is protected hydroxyl. In yet another embodiment, R⁸ includes a solid support. As a further example, in one embodiment R⁶ is a guanosine analog. An exemplary guanosine analog is shown in the compound of the formula (4f),

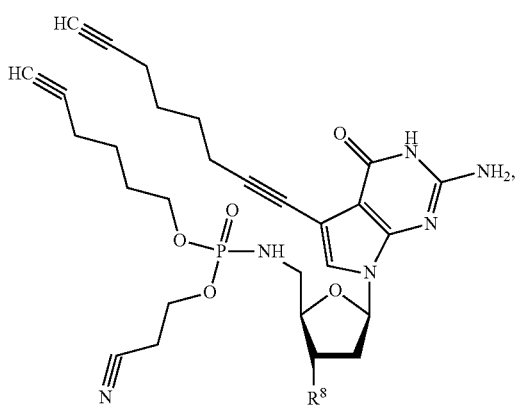

(4f)

wherein: G¹ is shown as cyanoethyl however other protecting groups may be substituted for cyanoethyl; R¹³ is shown as —C≡C—(CH$_2$)$_4$—C≡CH however other omega-functionalized C$_6$-C$_{16}$ hydrocarbon groups may be substituted for —C≡C—(CH$_2$)$_4$—C≡CH; R⁸ is —OR¹¹ or —O-L-SS where L-SS represents a solid support optionally bound to a linker; R¹¹ is selected from H and G³; and G³ is a protecting group for a hydroxyl group that is bonded to a carbon atom. In one embodiment, R⁸ is hydroxyl. In one embodiment, R⁸ is protected hydroxyl. In yet another embodiment, R⁸ includes a solid support.

The present disclosure also provides a cyclic phosphite of the formula (5) and salts thereof,

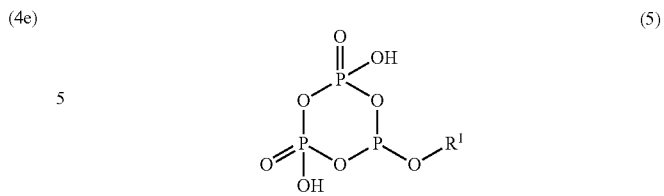

(5)

wherein R¹ is an alkyl group or an oxyalkyl group, either of which is terminally-functionalized, where the terminal functional group is selected from carbon-carbon double bond, carbon-carbon triple bond, hydroxyl, amine, azide, hydrazine, thiol, carboxyl or ester thereof, formyl, hydroxylamino and halogen. For example, in individual embodiments, the terminal functional group of R¹ may be carbon-carbon double bond; and/or it may be carbon-carbon triple bond; and/or it may be hydroxyl; and/or it may be amine; and/or it may be thiol; and/or it may be carboxyl or ester thereof; and/or it may be formyl; and/or it may be hydroxylamino; and/or it may be halogen. For example, when R¹ is an alkyl group and the functional group is a carbon-carbon triple bond, R¹ may be —(CH$_2$)$_q$—C≡CH where —(CH$_2$)$_q$ is the alkyl group, which might also be referred to as an alkylene group, and q is an integer selected from 2-10, e.g., R¹ is 1-hexynyl of the formula —CH$_2$CH$_2$CH$_2$CH$_2$C≡CH. In one embodiment, R¹ includes an electrophilic group. In one embodiment, R¹ includes a nucleophilic group. In one embodiment, R¹ includes a carboxylic acid or an ester thereof. In one embodiment, R¹ is an alkyl group which is terminally-functionalized. In one embodiment, R¹ is an oxyalkyl group which is terminally functionalized, where an oxyalkyl group may also be called an oxyalkylene group, and refers to an alkyl group that incorporates one or more oxygen atoms in the form of ether groups. Oxyethyl (—O—CH$_2$—CH$_2$—) groups and oxypropyl (—O—CH$_2$—CH$_2$—CH$_2$—) groups are exemplary oxyalkyl groups. The oxyalkyl group of R¹ may be formed from one or a plurality of oxyalkyl units, such as 2, 3, 4, 5, 6, 7, 8, 9, 10, or more than 10 repeating units.

In one embodiment, the present invention provides a process for forming an N-phosphoroamidate diester (110) as illustrated in Scheme 1.

Scheme 1

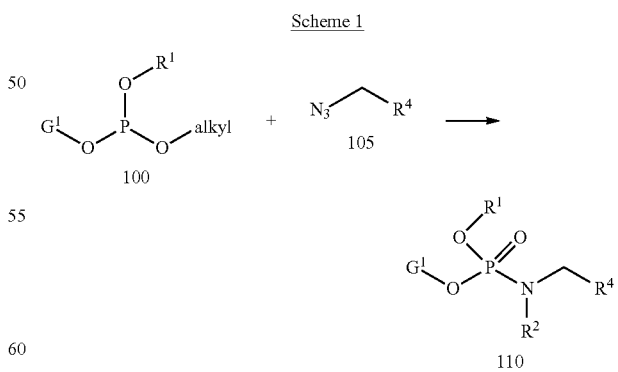

In Scheme 1, a suitably protected alkyl-substituted phosphite triester (100) is reacted with an azide (105) in a solvent and in the presence of a halide anion source such as lithium chloride to form a N-phosphoroamidate diester (110) where G¹ is H or a protecting group and R² is hydrogen.

Thus, in one embodiment, the present disclosure provides a process of forming a phosphoromonoamidate diester 110 from a phosphite triester compound (100) and an azide compound (105),

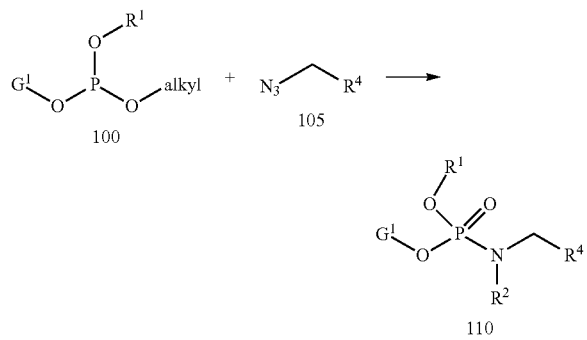

the process comprising combining (100) with (105) in the presence of a halide anion, such as lithium chloride, in a suitable solvent such as dimethylsulfoxide, at a suitable reaction temperature such as about 55° C., and for a suitable time period such as about 24-36 hours, wherein:

$R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^2$ is selected from hydrogen and $C_1$-$C_4$alkyl;

$R^4$ is selected from

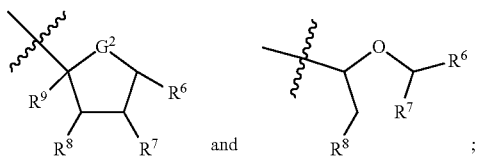

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and $CH_2$; and $G^3$ is a protecting group for a hydroxyl group that is bonded to a carbon atom.

As illustrated in Scheme 2, the protected phosphite (100) may be synthesized from the corresponding N,N-diisopropylphosphoramidite (90), where (90) may be obtained from commercial sources (for example, from Chemgenes of Wilmington, Mass., USA or Berry and Associates of Dexter, Mich., USA) or synthesized by methods known in the art. The reaction of compound (90) with an alcohol (HO-alkyl) in the presence of a suitable activator such as 1H-tetrazole in a suitable solvent such as acetonitrile provides the protected phosphite (100). Activators, sometimes referred to as coupling activators, are known in the art of phosphoramidite chemistry and oligonucleotide synthesis, where other suitable activators include 5-ethylthio-1H-tetrazole, 5-benzylthio-1H-tetrazole and 4,5-dicyanoimidazole, each available from, e.g., Glen Research (Sterling, Va.). See also, for example, Dahl, B. H., et al. Nucleic Acids Res (1987) 15:1729-43; Vargeese, C. et al., Nucl. Acids Res. (1998) 26 (4):1046-1050; and Berner, S., Nucleic Acids Res. (1989) 17:853-64. Benzimidazolium triflate may also be used as an activator, see, e.g., Hayakawa Y., et al., J. Org. Chem. (1996) 61:7996-7997.

Scheme 2

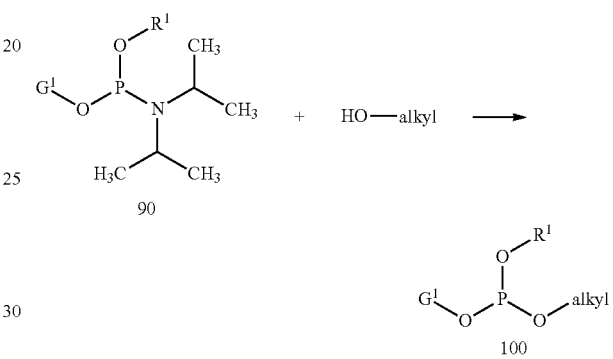

Thus, in another embodiment, the present disclosure provides a process wherein compound 100 is prepared from reaction of compound 90 and an alcohol of formula HO-alkyl where the reaction is conducted in the presence of an activator.

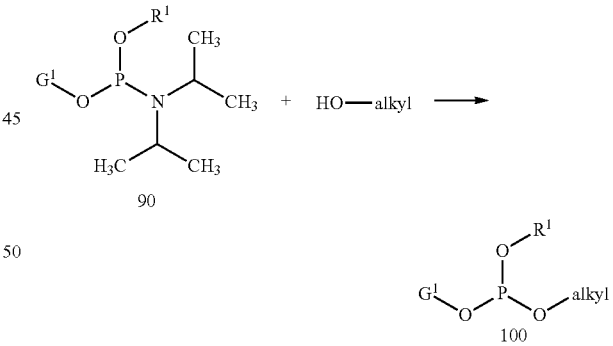

The azide (105) from Scheme 1 may be prepared from the corresponding iodo compound (85), which in turn may be prepared from the corresponding protected hydroxyl compound (80) as illustrated in Scheme 3.

Scheme 3

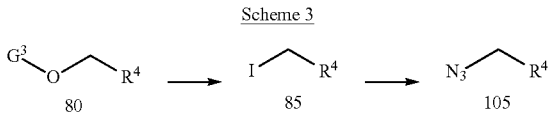

In Scheme 3, the protected hydroxyl compound (80) may be converted to the corresponding iodo compound (85) by a two-step reaction. In the first step, the protecting group $G^3$ is removed under conditions that are appropriate for that particular protecting group. For example, if the protecting group $G^3$ is dimethoxytrityl ether (DMTr) then $G^3$ can be removed by treatment with 3% trichloroacetic acid (TCA) in a suitable solvent such as methylene chloride to provide the free hydroxyl compound, i.e., $G^3$ is hydrogen. In the second step, the free hydroxyl compound is reacted with methyltriphenoxyphosphonium iodide in a suitable solvent such as dimethylformamide to provide the corresponding iodo compound (85). The iodo compound (85) may be readily converted to the corresponding azide (105) by treatment with sodium azide in a suitable solvent, such as dimethylformamide.

Thus, in another embodiment, the present disclosure provides a process wherein compound 80 is converted to compound 85 and compound 85 is converted to compound 105

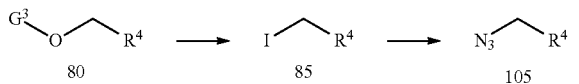

where $G^3$ is removed under conditions that are appropriate for that particular protecting group to provide the corresponding free hydroxyl compound, i.e., $G^3$ is hydrogen; and the free hydroxyl compound is reacted with methyltriphenoxyphosphonium iodide in a suitable solvent to provide the corresponding iodo compound (85), and the iodo compound (85) is converted to the corresponding azide (105) by treatment with sodium azide in a suitable solvent.

In one embodiment, the present invention provides a process for forming a phosphate protected N-phosphoroamidate-monoester diphosphate (120) as illustrated in Scheme 4.

Scheme 4

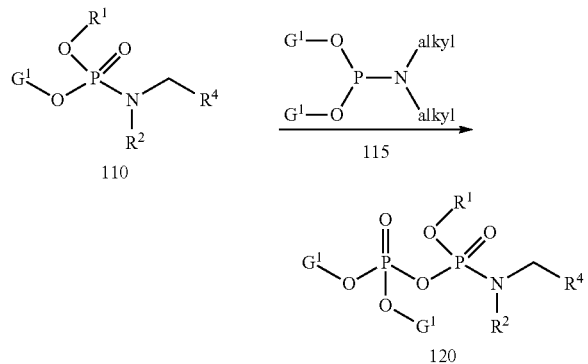

In Scheme 4, a suitably protected N-phosphoroamidate diester (110) is reacted with a base such as 1,8-diazabicyclo[5.4.0]undec-7-ene (DBU) in the presence of a silylating agent such as N,O-bis-trimethylsilylacetamide (BSA) to form a first intermediate (not shown in Scheme 4) which is subsequently reacted, optionally and preferably without isolation, with a phosphorylating agent such as the phosphorylating phosphoramidite (115, available commercially from, e.g., Chemgenes, Wilmington, Mass., USA) as shown in Scheme 4, in the presence of an activator such as 5-(ethylthio)-1H-tetrazole (ETT) to form a second intermediate (not shown in Scheme 4) which is subsequently reacted, optionally and preferably without isolation, with an oxidizing agent such as an organic peroxide such as t-butylhydroperoxide in a suitable solvent such as methylene chloride to form the phosphate protected N-phosphoroamidate-monoester diphosphate (120).

Thus, in one embodiment, the present disclosure provides a process of forming a phosphate protected N-phosphoroamidate-monoester disphosphate (120) from a phosphoroamidate diester compound (110) and a phosphorylating phosphoramidite compound 115,

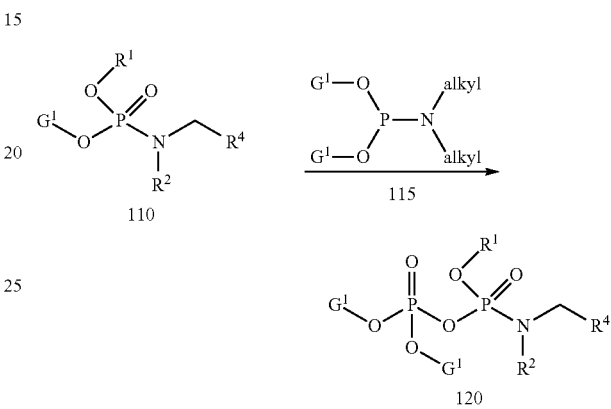

the process comprising combining (110) with a base and a silylating agent to provide a first intermediate, combining the first intermediate with (115) and an activator to provide a second intermediate, and combining the second intermediate with an oxidizing agent to form the phosphate protected N-phosphoroamidate-monoester diphosphate (120), wherein:

$R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^2$ is selected from hydrogen and $C_1$-$C_4$alkyl;

$R^4$ is selected from

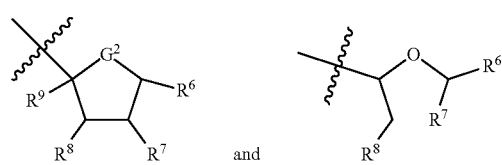

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and $CH_2$; and $G^3$ is a protecting group for a hydroxyl group that is bonded to a carbon atom.

In one embodiment, the present invention provides a process for forming a phosphate protected N-phosphoroamidate-monoester triphosphate (125) as illustrated in Scheme 5.

Scheme 5

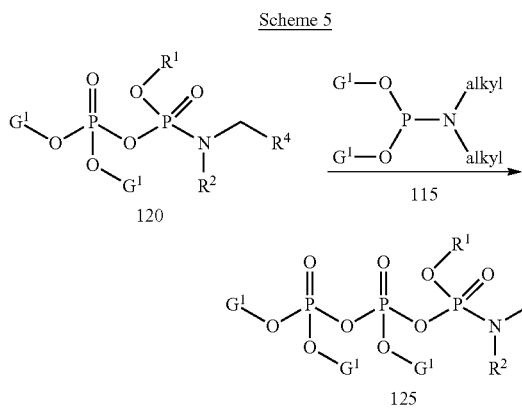

In Scheme 5, a suitably protected phosphate protected N-phosphoroamidate-monoester diphosphate (120) is reacted with a base such as DBU and a silylating agent such as BSA to form a first intermediate (not shown in Scheme 5) which is subsequently reacted, optionally and preferably without isolation, with a phosphorylating agent such as the phosphorylating phosphoramidite (115) as shown in Scheme 5, in the presence of an activator such as ETT to form a second intermediate (not shown in Scheme 5) which is subsequently reacted, optionally and preferably without isolation, with an organic peroxide such as t-butylhydroperoxide in a suitable solvent such as methylene chloride to form the phosphate protected N-phosphoroamidate-monoester triphosphate (125).

Thus, in one embodiment, the present disclosure provides a process of forming a phosphate protected N-phosphoroamidate-monoester triphosphate (125) from a phosphate protected N-phosphoroamidate-monoester diphosphate compound (120) and a phosphorylating phosphoramidite compound (115),

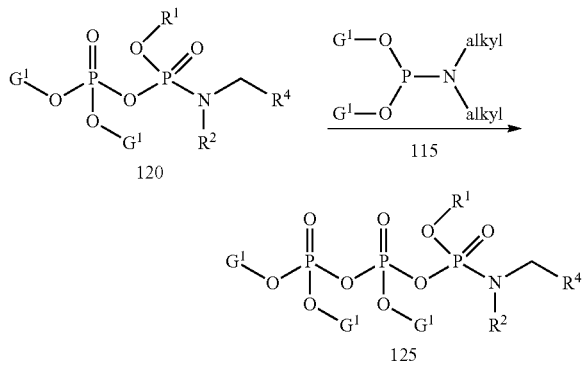

the process comprising combining (120) with a base and a silylating agent to provide a first intermediate, combining the first intermediate with (115) and an activator to provide a second intermediate, and combining the second intermediate with an oxidizing agent to form the phosphate protected N-phosphoroamidate-monoester triphosphate (125), wherein $R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^2$ is selected from hydrogen and $C_1$-$C_4$alkyl;

$R^4$ is selected from

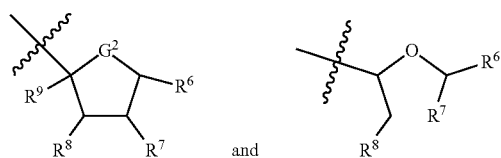

and ;

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and $CH_2$; and $G^3$ is a protecting group for a hydroxyl group that is bonded to a carbon atom.

The phosphate protected N-phosphoroamidate-monoester triphosphate (125), which may be prepared as shown in Scheme 5, comprises protecting groups $G^1$, and may include a solid support SS through $R^8$ of $R^4$. In one embodiment, phosphate protected N-phosphoroamidate-monoester triphosphate (125) is exposed to conditions suitable for removing the protecting groups $G^1$ and cleaving the linker of the solid support if present. The choice of suitable conditions will depend on the identity of the protecting groups and the linking group that have been employed to make (125). In the case where the protecting groups are base labile, e.g., trimethylsilyl groups, and the linker is base labile, e.g., $R^8$ is SS—NH—(C═O)—$CH_2$—O—Ar—O—$CH_2$C(═O)—O—, then treatment of protected and support-bound (125) with concentrated ammonium hydroxide at room temperature for about 5 minutes will release the phosphoramidite from the solid support and remove the protecting groups $G^1$. In the exemplary case where $R^2$ is hydrogen, $G^2$ is oxygen, and $R^4$ represents a cyclic sugar, these reaction conditions will provide (130), (130)

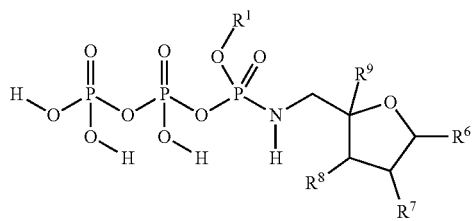

wherein $R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —CH$_2$-halogen, $C_1$-$C_4$alkyl, hydroxyl and —CH$_2$—OR$^{10}$;

$R^8$ is —OR$^{11}$;

$R^9$ is hydrogen or, when $R^7$ is —CH$_2$—OR$^{10}$ then $R^9$ may be —CH$_2$—R$^{12}$ where $R^{10}$ and $R^{12}$ form a direct bond; and $R^{11}$ is hydrogen.

As described elsewhere herein, in one embodiment the present invention provides a process for forming a compound (130) by deprotecting a compound (125), where compound (125) may be synthesized as shown in Scheme 5. In another embodiment, the present disclosure provides an alternative process for forming a compound (130) which is illustrated in Schemes 6-8.

In Scheme 6, a cyclic phosphite (145) is prepared from an alcohol $R^1$—OH (compound 140), e.g., 5-hexyn-1-ol, and commercially available 2-chloro-4H-1,3,2-benzodioxaposphorin-4-one (compound 135) by combining these reactants in a suitable solvent such a dimethylformamide and in the presence of a suitable base such as tributylamine, at a suitable reaction temperature such as about room temperature, for a suitable period of time such as for about 5-60 minutes, to prepare compound 145, e.g., salicyl-(5-hexyn-1-yl) phosphite. Suitable reaction conditions are disclosed in, e.g., Ludwig and Eckstein, J. Org. Chem. 56:1777-1783 (1991).

Scheme 6

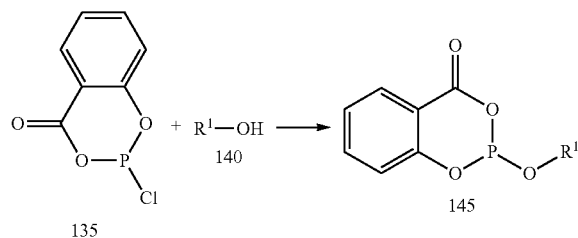

The product (145) from Scheme 6 may be added to commercially available 0.5M bis-tributylammonium pyrophosphate (150) in a suitable solvent, such as dimethylformamide, at a suitable temperature such as about room temperature, and for a suitable period of time, such as for 5-60 minutes, to provide the salt of the cyclotriphosphite compounds (155), as illustrated in Scheme 7.

Scheme 7

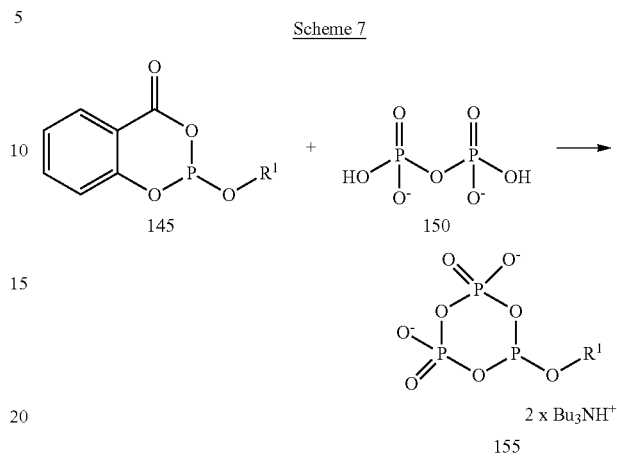

The cyclotriphosphite (155) may be reacted with previously described azide (105) under suitable reaction conditions such as in a suitable solvent such as dimethylsulfoxide, at a suitable reaction temperature such as about 55° C., and for a suitable time period such as about 24-36 hours, as shown in Scheme 8, Scheme 8

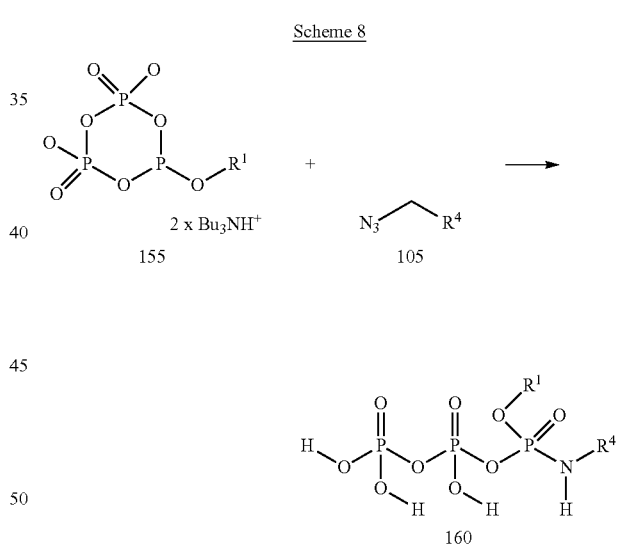

In the case were the reactions illustrated in Schemes 6, 7 and 8 are conducted on a solid support, i.e., where $R^4$ includes a solid support as part of $R^8$, then the linkage to the solid support may be cleaved under suitable reaction conditions. For example, if a base labile linker is present, such as when $R^8$ is SS—NH—(C=O)—CH$_2$—O—Ar—O—CH$_2$C(=O)—O—, then treatment of support-bound (160) with concentrated ammonium hydroxide at room temperature for about 5 minutes will release the phosphoramidite from the solid support. In the exemplary case where $R^2$ is hydrogen, $G^2$ is oxygen, and $R^4$ represents a cyclic sugar, these reaction conditions provide an alternative route to compound (130),

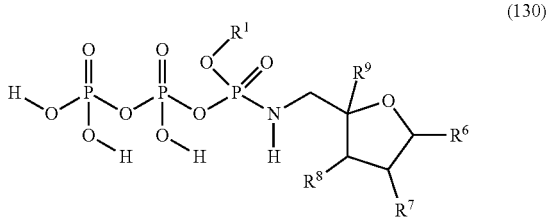

(130)

wherein $R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl, hydroxyl and —$CH_2$—$OR^{10}$;

$R^8$ is —$OR^{11}$;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond; and $R^{11}$ is hydrogen.

Thus, in one embodiment the present disclosure provides a process for forming a N-phosphoroamidate-monoester triphosphate (160) from a cyclotriphosphate (155) and an azide (105)

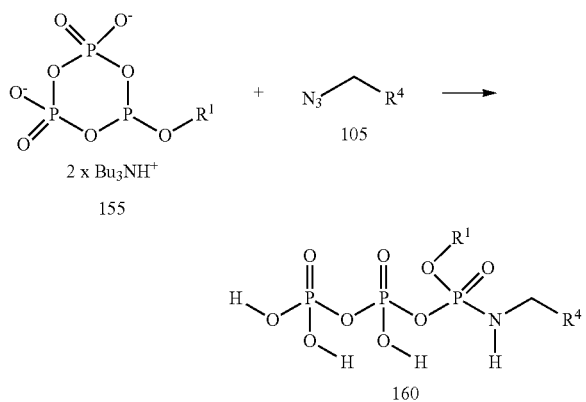

the process comprising combining (155) and (105) in the presence of solvent so as to form (160), wherein:

$R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^4$ is selected from

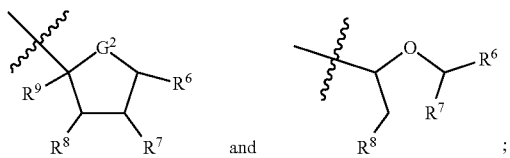

$R^6$ is a heterocycle, optionally substituted with $R^{13}$, where $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^2$ is selected from oxygen, sulfur and $CH_2$; and $G^3$ is a protecting group for a hydroxyl group that is bonded to a carbon atom.

In the foregoing Schemes 1-8, and within the disclosure as provided herein, the $R^8$ group may be or includes a solid support, so that, for example, one or more of, and preferably all of, the conversion of compound (80) to compound (85), the conversion of compound (85) to (105), the conversion of compound (105) to compound (110), and the conversion of compound (155) to compound (160) is performed using solid phase synthesis techniques.

Stratos Genomics has developed a method called Sequencing by Expansion ("SBX") that uses a biochemical process to transcribe the sequence of DNA onto a measurable polymer called an "Xpandomer" (Kokoris et al., U.S. Pat. No. 7,939,259, "High Throughput Nucleic Acid Sequencing by Expansion"). The transcribed sequence is encoded along the Xpandomer backbone in high signal-to-noise reporters that are separated by ~10 nm and are designed for high-signal-to-noise, well-differentiated responses. These differences provide significant performance enhancements in sequence read efficiency and accuracy of Xpandomers relative to native DNA. Xpandomers can enable several next generation DNA sequencing detection technologies and are well suited to nanopore sequencing. The compounds as disclosed herein, and the synthetic methods as disclosed herein, may be used in carrying out SBX.

Xpandomers are generated from polymerization of non-natural nucleotide analogs, termed XNTPs, which are expandable, 5' triphosphate modified nucleotide substrates compatible with template dependent enzymatic polymerization. An XNTP has two distinct functional regions; namely, a nucleoside triphosphoramidate and a tether that is attached within each nucleoside triphosphoramidate at positions that allow for controlled expansion by intra-nucleotide cleavage of the phosphoramidate bond. XNTPs are described in the FIGURE in more detail.

As depicted in the FIGURE, the XNTP 100 is comprised of nucleobase triphosphoramidate 110 with linker arm moieties 120A (which is shown as a $C_4$ hydrocarbon chain that is a part of $R^1$ as disclosed herein) and 120B (which is shown as a $C_6$ hydrocarbon chain that is part of $R^{13}$ as disclosed herein) separated by selectively cleavable phosphoramidate bond 130. Each linker 120A and 120B attaches to one end of tether 140 via a linking group (LG), as disclosed in U.S. Pat. No. 8,324,360 to Kokoris et al., which is herein incorporated by reference in its entirety. Tethers are polymers or molecular constructs having a generally linear dimension and with an end moiety at each of two opposing ends which are attached to the nucleobase triphosphoramidate 110 via the reaction products of the terminal functional groups of $R^1$ and $R^{13}$ to form the XNTP 100. XNTPs have a "constrained configuration" and an "expanded configuration". The constrained configuration is found in XNTPs and in the daughter strand. The constrained configuration of the XNTP is the precursor to the expanded configuration, as found in Xpandomer products. The transition from the constrained configuration to the expanded configuration occurs upon scission of the P—N bond 130 of the phosphoramidate within the primary backbone of the daughter strand.

Tethers are joined to the nucleoside triphosphoramidate at linking group 150A and 150B, wherein a first tether end is joined to the heterocycle (represented in the FIGURE by the symbol "$B_{1-4}$", wherein the subscript indicates that the heterocycle may be any one of the four standard nucleobases, A, C, G, or T) and the second tether end is joined to the alpha phosphate of the nucleobase backbone. For example, to synthesize a XATP monomer, the amino linker on 7-(octa-1,7-dinyl)-7-deaza-2'-dATP can be used as a first tether attachment point, and a mixed backbone linker, such as the non-bridging modification (N–1-aminoalkyl) phosphoramidate can be used as a second tether attachment point. The skilled artisan will appreciate that many suitable coupling chemistries known in the art may be used to form the final XNTP substrate product, for example, tether conjugation may be accomplished through a triazole linkage.

Thus, the present disclosure provides a process in which an N-phosphoroamidate-monoester triphosphate (160) as described previously is reacted with a tether precursor of the formula X-T-X where X represents a reactive functional group that is reactive with the terminating functional groups of $R^1$ and $R^{13}$, so as to form linker groups LG1 and LG2. Optionally, X-T-X may be a bis-azido compound of the formula $N_3$-T-$N_3$, and the terminating functional groups of $R^1$ and $R^{13}$ are alkyne groups, so as to form triazole groups LG1 and LG2.

After the tether has been joined to the phosphoramidate, the resulting compound is an XNTP of the formula

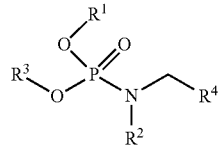

wherein
$R^1$ is selected from an alkyl group and an oxyalkyl group, either of which terminates in a linker group (LG1), the LG1 bonded to a tether (T);
$R^2$ is selected from hydrogen and $C_1$-$C_4$alkyl;
$R^3$ is selected from $R^5$ and —[Pn-O]$_m$—$R^5$, where Pn is independently selected from P(O$R^5$) and P(=O)(O$R^5$) at each occurrence, and m is selected from 1, 2, 3, 4, 5 and 6;
$R^4$ is selected from

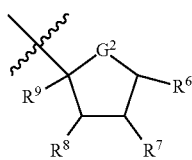 and 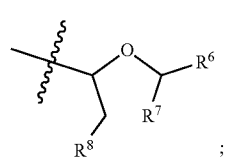 ;

$R^5$ is selected from H and $G^1$;
$R^6$ is a heterocycle, the heterocycle comprising a substituent $R^{13}$, where $R^{13}$ is selected from an alkyl group and an oxyalkyl group, either of which terminates in a linker group (LG2), the LG2 bonded to the tether (T);
$R^7$ is selected from hydrogen, —CH$_2$-halogen, $C_1$-$C_4$alkyl, hydroxyl and —CH$_2$—OR$^{10}$;
$R^8$ is —OR$^{11}$ or —O-L-SS where L-SS represents a solid support optionally bound to a linker;
$R^9$ is hydrogen or, when $R^7$ is —CH$_2$—OR$^{10}$ then $R^9$ may be —CH$_2$—$R^{12}$ where $R^{10}$ and $R^{12}$ form a direct bond;
$R^{11}$ is selected from H and $G^3$;
$G^1$ is H or a protecting group for a hydroxyl group that is bonded to a phosphorous atom;
$G^2$ is selected from oxygen, sulfur and CH$_2$; and
$G^3$ is a protecting group for a hydroxyl group that is bonded to a carbon atom.

In optional embodiments of the XNTP, which are exemplary only of XNTP embodiments as provided herein, and any of which may be combined, the present disclosure provides embodiments wherein:
(a) $R^1$ is an alkyl group which terminates in a linker group (LG1), the LG1 bonded to a tether (T);
(b) $R^1$ is an oxyalkyl group which terminates in a linker group (LG1), the LG1 bonded to a tether (T);
(c) $R^2$ is hydrogen;
(d) $R^3$ is $R^5$;
(e) $R^3$ is —[Pn-O]$_m$—$R^5$, where Pn is independently selected from P(O$R^5$) and P(=O)(O$R^5$) at each occurrence, and m is selected from 1, 2, 3, 4, 5 and 6, or m is selected from 2, 3, 4, 5 and 6; or m is 2; or m is 3; or m is 4; or m is 5; or m is 6;
(f) $R^3$ is —[Pn-O]$_n$—$R^5$, where Pn is P(=O)(O$R^5$) at each occurrence, and m is selected from 1, 2, 3, 4, 5 and 6, or m is selected from 2, 3, 4, 5 and 6; or m is 2; or m is 3; or m is 4; or m is 5; or m is 6;
(g) $R^4$ is

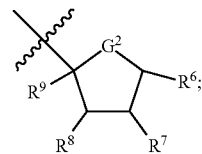

(h) $R^4$ is

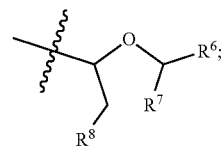

(i) $R^5$ is H;
(j) $R^6$ is a heterocycle, the heterocycle comprising a substituent $R^{13}$, where $R^{13}$ is an alkyl group which terminates in a linker group (LG2), the LG2 bonded to the tether (T);
(k) $R^6$ is a heterocycle, the heterocycle comprising a substituent $R^{13}$, where $R^{13}$ is an oxyalkyl group which terminates in a linker group (LG2), the LG2 bonded to the tether (T);
(l) $R^7$ is hydrogen;
(m) $R^7$ is —CH$_2$-halogen;
(n) $R^7$ is $C_1$-$C_4$alkyl;
(o) $R^7$ is hydroxyl;
(p) $R^7$ is —CH$_2$—OR$^{10}$;

(q) $R^8$ is —$OR^{11}$;
(r) $R^8$ is —O-L-SS where L-SS represents a solid support optionally bound to a linker;
(s) $R^9$ is hydrogen;
(t) $R^9$ is —$CH_2$—$R^{12}$ where $R^{10}$ and $R^{12}$ form a direct bond;
(u) $R^{11}$ is H;
(v) $R^{11}$ is $G^3$;
(w) $G^1$ is H;
(x) $G^1$ is a protecting group for a hydroxyl group that is bonded to a phosphorous atom;
(y) $G^2$ is oxygen;
(z) LG1 and LG2 are each triazole.

During assembly, the monomeric XNTP substrate construct is polymerized on the extendable terminus of the nascent daughter strand by a process of template-directed polymerization using a single-stranded template as a guide. Generally, this process is initiated from a primer and proceeds in the 5' to 3' direction. Generally, a DNA polymerase or other polymerase is used to form the daughter strand, and conditions are selected so that a complementary copy of the template strand is obtained.

As mentioned previously, further details may be found in International Patent Application No. PCT/US2015/03079 and U.S. Pat. No. 8,324,360. For example, as explained in U.S. Pat. No. 8,324,360, a "tether" or "tether member" refers to a polymer or molecular construct having a generally linear dimension and with an end moiety at each of two opposing ends. A tether is attached to a substrate with a linkage in at least one end moiety to form a substrate construct. The end moieties of the tether may be connected to cleavable linkages to the substrate or cleavable intra-tether linkages that serve to constrain the tether in a "constrained configuration". After the daughter strand is synthesized, each end moiety has an end linkage that couples directly or indirectly to other tethers. The coupled tethers comprise the constrained Xpandomer that further comprises the daughter strand. Tethers have a "constrained configuration" and an "expanded configuration". The constrained configuration is found in substrate constructs and in the daughter strand. The constrained configuration of the tether is the precursor to the expanded configuration, as found in Xpandomer products. The transition from the constrained configuration to the expanded configuration results cleaving of selectively cleavable bonds that may be within the primary backbone of the daughter strand or intra-tether linkages. A tether in a constrained configuration is also used where a tether is added to form the daughter strand after assembly of the "primary backbone". Tethers can optionally comprise one or more reporters or reporter constructs along its length that can encode sequence information of substrates. The tether provides a means to expand the length of the Xpandomer and thereby lower the sequence information linear density "Tether constructs" are tethers or tether precursors composed of one or more tether segments or other architectural components for assembling tethers such as reporter constructs, or reporter precursors, including polymers, graft copolymers, block copolymers, affinity ligands, oligomers, haptens, aptamers, dendrimers, linkage groups or affinity binding group (e.g., biotin).

"Tether element" or "tether segment" (T) is a polymer having a generally linear dimension with two terminal ends, where the ends form end-linkages (LG1 and LG2) for concatenating the tether elements. A precursor to such a tether element may have the formula X-T-X wherein T represents the tether element and X is a reactive functional group that will react so as to form end-linkages LG1 and LG2, where LG1 and LG2 are also joined to a nucleobase triphosphoramidate, and are shown in the FIGURE as 150B and 150A, respectively. Tether elements may be segments of tether constructs. Such polymers can include, but are not limited to: polyethylene glycols, polyglycols, polypyridines, polyisocyanides, polyisocyanates, poly(triarylmethyl)methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments.

Reporter element" is a signaling element, molecular complex, compound, molecule or atom that is also comprised of an associated "reporter detection characteristic". Other reporter elements include, but are not limited to, FRET resonant donor or acceptor, dye, quantum dot, bead, dendrimer, upconverting fluorophore, magnet particle, electron scatterer (e.g., boron), mass, gold bead, magnetic resonance, ionizable group, polar group, hydrophobic group. Still others are fluorescent labels, such as but not limited to, ethidium bromide, SYBR Green, Texas Red, acridine orange, pyrene, 4-nitro-1,8-naphthalimide, TOTO-1, YOYO-1, cyanine 3 (Cy3), cyanine 5 (Cy5), phycoerythrin, phycocyanin, allophycocyanin, FITC, rhodamine, 5(6)-carboxyfluorescein, fluorescent proteins, DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (Biological Detection Systems, Inc.), erytrosine, coumaric acid, umbelliferone, texas red rhodaine, tetramethyl rhodamin, Rox, 7-nitrobenzo-1-oxa-1-diazole (NBD), oxazole, thiazole, pyrene, fluorescein or lanthamides; also radioisotopes, ethidium, Europium, Ruthenium, and Samarium or other radioisotopes; or mass tags, such as, for example, pyrimidines modified at the C5 position or purines modified at the N7 position, wherein mass modifying groups can be, for examples, halogen, ether or polyether, alkyl, ester or polyester, or of the general type XR, wherein X is a linking group and R is a mass-modifying group, chemiluminescent labels, spin labels, enzymes (such as peroxidases, alkaline phosphatases, beta-galactosidases, and oxidases), antibody fragments, and affinity ligands (such as an oligomer, hapten, and aptamer). Association of the reporter element with the tether can be covalent or non-covalent, and direct or indirect. Representative covalent associations include linker and zero-linker bonds. Included are bonds to the tether backbone or to a tether-bonded element such as a dendrimer or sidechain. Representative non-covalent bonds include hydrogen bonds, hydrophobic bonds, ionic bonds, pi-bond ring stacking, Van der Waals interactions, and the like. Ligands, for example, are associated by specific affinity binding with binding sites on the reporter element. Direct association can take place at the time of tether synthesis, after tether synthesis, and before or after Xpandomer synthesis.

A "reporter" is composed of one or more reporter elements. Reporters include what are known as "tags" and "labels." The probe or nucleobase residue of the Xpandomer can be considered a reporter. Reporters serve to parse the genetic information of the target nucleic acid.

"Reporter construct" comprises one or more reporters that can produce a detectable signal(s), wherein the detectable signal(s) generally contain sequence information. This signal information is termed the "reporter code" and is subsequently decoded into genetic sequence data. A reporter construct may also comprise tether segments or other architectural components including polymers, graft copolymers, block copolymers, affinity ligands, oligomers, haptens, aptamers, dendrimers, linkage groups or affinity binding group (e.g., biotin).

The Examples and preparations provided below further illustrate and exemplify the compounds of the present invention and methods of preparing such compounds. It is to be understood that the scope of the present invention is not limited in any way by the scope of the following Examples and preparations. In the following Examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art. The starting materials and various reactants utilized or referenced in the examples may be obtained from commercial sources, or are readily prepared from commercially available organic compounds, using methods well-known to one skilled in the art.

EXAMPLES

Materials and General Methods:

The following materials, having the abbreviations as indicated, were obtained from the mentioned sources in the United States, unless otherwise indicated. Aminopropyl-CPG 500A, 120-200 mesh (Prime Synthesis, Inc., Aston, Pa.). HQDA (1) (Hydroquinone-O,O'-diacetic acid, Alfa Aesar, Ward Hill, Mass.). DMAP (4-Dimethylamino pyridine, TCI America, Portland, Oreg.). Bis-CNET (Bis-cyanoethyl-N,N-diisopropylphosphoramidite, ChemGenes, Wilmington, Mass.). BSA (N,O-bis(trimethylsilyl)acetamide) (Acros Organics, NJ). HBTU (1H-benzotriazol-1-yl)-1,1,3,3-tetramethyluronium hexafluorophosphate (EMD Millipore, Billerica, Mass.). Methyltriphenoxyphosphonium iodide (Toronto Research Chemicals, Toronto, ON CANADA). 5'-O-Dimethoxytrityl-5-(octa-1,7-diynyl)-2'-deoxyuridine (3) (ChemBiotech, Munster, Germany). 0.5M Bis-tributylammonium pyrophosphate in DMF (15, GL Synthesis Inc., Worcester, Mass.). 5'-hexynyl phosphoramidite (5-hexyn-1-yl-(2-cyanoethyl)-(N,N-diisopropyl)-phosphoramidite) from Glen Research, Inc., Sterling, Va. ETT (5-Ethylthio-1H-tetrazole), from Glen Research, Inc., Sterling, Va. LiCl (lithium chloride), DIEA (diisopropylethylamine), DBU (1,8-diazabicyclo[5.4.0]undec-7-ene, TBHP (t-butylhydroperoxide), DCM (dichloromethane), ACN (acetonitrile) and DMF (dimethylformamide) may each be obtained from Sigma, St. Louis, Mo. 2-chloro-4H-1,3,2-benzodioxaphosphorin-4-one (salicyl chlorophosphite) (12); and 5-hexyn-1-ol (13) may also be obtained from Sigma, St. Louis, Mo. Solvents are anhydrous and packaged in Sure-Seal™ containers or equivalent. 2M triethylammonium acetate, $Pac_2O$ Cap A (5% (w/v) phenoxyacetic anhydride: 10% pyridine in THF, and $Pac_2O$ Cap B (16% 1-methylimidazole in THF may each be obtained from Glen Research, Sterling, Va.

High performance liquid chromatography is performed on a ProStar Helix™ HPLC system from Agilent Technologies, Inc. (Santa Clara, Calif.) consisting of two pumps (ProStar 210 Solvent Delivery Modules) with 10 ml titanium pump heads, a column oven (ProStar 510 Air Oven), a UV detector (ProStar 320 UV/Vis Detector) set at 292 nm. The system is controlled by Star Chromatography Workstation Software (Version 6.41). The column used is a Cadenza CD-C18, 3 µm (4.6 mm×150 mm) equipped with an in-line Cadenza Guard Column System for CD-C18 (2.0 mm×5 mm) both from Imtakt USA (Portland, Oreg.). The buffers used are: Buffer A (100 mM triethylammonium acetate, pH 7.0) and Buffer B (100 mM triethylammonium acetate, pH 7.0 with 95% by volume acetonitrile).

Automated solid phase synthesis was done on a MerMade™ 12 Synthesizer (Bioautomation Corp., Plano, Tex.). Synthesis solutions for the MerMade™ 12 were purchased from Glen Research (Sterling, Va.).

ESI Mass spectrometry was done by Numega Resonance Lab (San Diego, Calif.). Mass specs on CPG-bound intermediates were performed on the products recovered after deprotection and cleavage off of the solid support. All ESI MS (positive mode) were consistent with the fully deprotected structures.

Synthetic Scheme A provides an outline of a methodology according to the present disclosure which is described in more detail in numbered Examples 1-8. The compounds 1-10 from Scheme A were used and/or synthesized in a glove box in a positive pressure argon atmosphere.

In Scheme A, the solid support is controlled pore glass (CPG), where CPG is an exemplary solid support of the present disclosure. Controlled pore glass (CPG) optionally, and typically does, include one or more of a plurality of reactive functional groups which may be reacted with a linking group precursor (e.g., HQDA, (1) as shown in Scheme A) to provide compound (2). The compound (2) is then coupled, or in other words linked, to a precursor of the compounds of the present disclosure, in this case through the hydroxyl group of a pentose ring of (3), to provide compound (4). Compound (4) is shown as including an exemplary solid support SS, namely CPG, and an exemplary linking group L, in this case presented by "Q", where Q represents propyl-NH—C(=O)—$CH_2$—O—Ar—O—$CH_2$—C(=O)—. Other reactive solid supports suitable for use in the present disclosure are known to the skilled person, and many of them are commercially available.

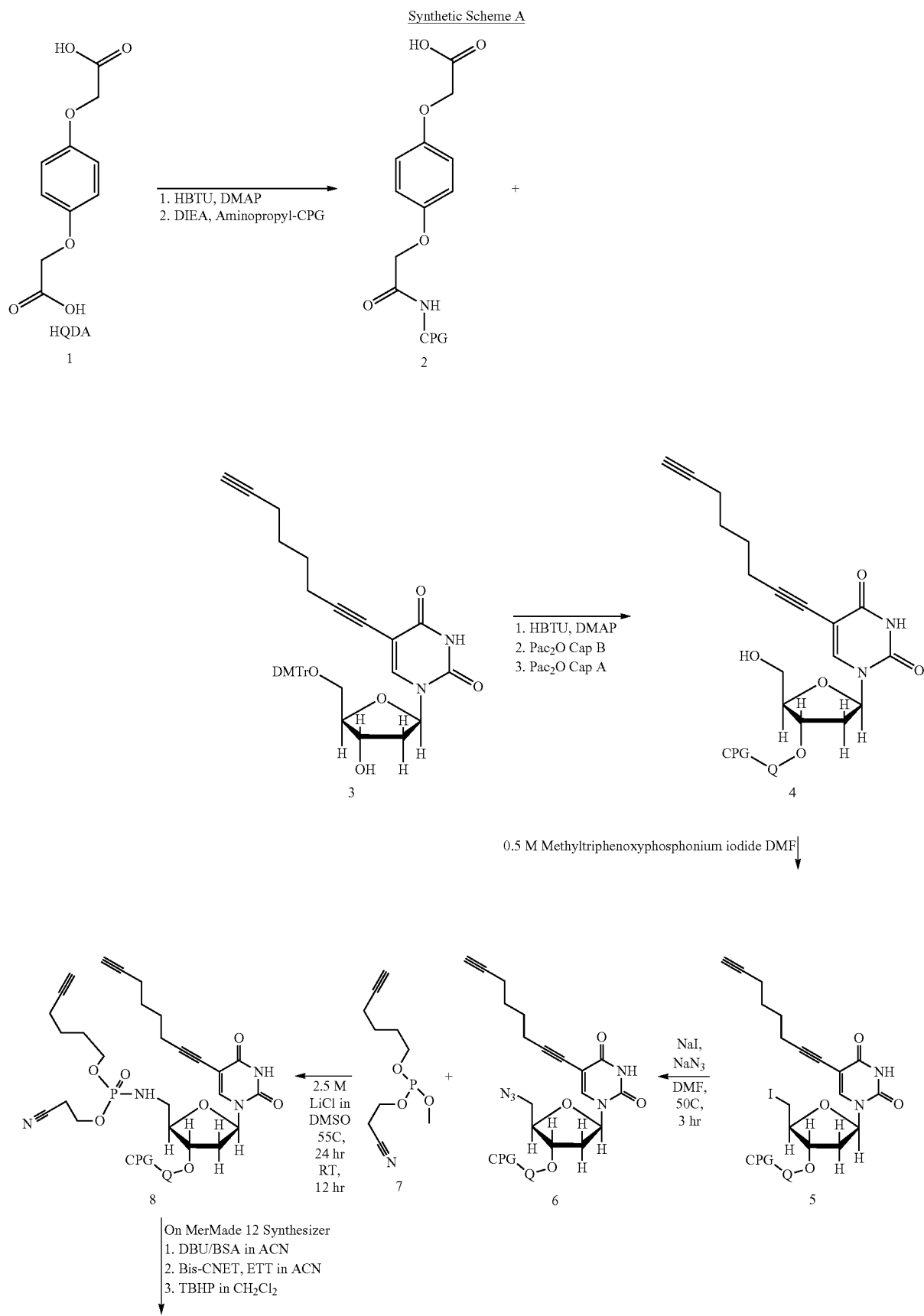

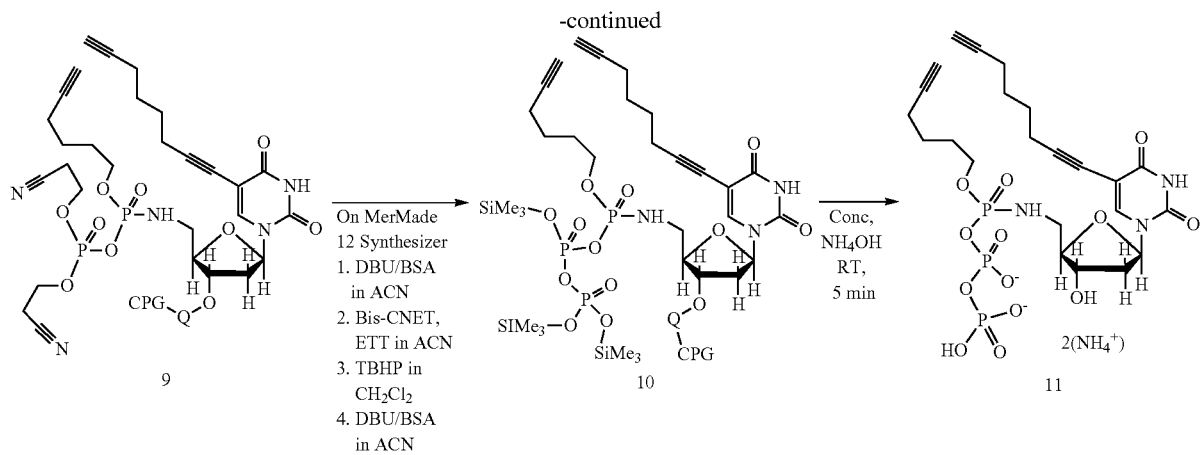

Example 1

HQDA-CPG (2)

HQDA-CPG (2) was prepared according to the method of Pon et. al., "Rapid Esterification of Nucleosides to Solid-Phase Supports for Oligonucleotide Synthesis Using Uronium and Phosphonium Coupling Reagents," Bioconjugate Chemistry, 10(6), 1051-1057 (1999). Aminopropyl-CPG (1, 1 g, 213 µmol amine) was transferred into a fritted 20 mL syringe and washed with acetonitrile (3×5 mL). DMAP (65.1 mg, 532 µmol) and HBTU (202 mg, 532 µmop were combined in a 8 mL polypropylene screw capped tube and mixed with acetonitrile (5 mL). To this tube was added HQDA (120.4 mg, 532 µmol) and DIEA (186 µL, 1065 µmol). A chalky precipitate formed and was removed by centrifugation and decanting the supernatant. The supernatant was added to the CPG in the fritted syringe. The syringe was capped on both ends and mixed on an inverting rotator for 2 hours. The syringe was mounted on a vacuum manifold equipped with a stopcock, drained and sequentially washed with acetonitrile (3×5 mL), methanol (2×5 mL), acetonitrile (2×5 mL) and methylene chloride (2×5 mL) to provide the title compound (2) in pure form. Confirmation of the HQDA coupling on the CPG was based on step trityl cation color formation as described in the following Example 2.

Example 2

5-(Octa-1,7-diynyl)-2'-deoxyuridine-3'-O-HQDA-CPG (4)

To a 8 mL polypropylene tube was added HBTU (121 mg, 319 µmol), DMAP (39 mg, 319 µmop and 5'-O-dimethoxytriyl-5-(octa-1,7-diynyl)-2'-deoxyuridine (3) (216 mg, 319 µmop dissolved in acetonitrile (4.8 mL). This solution was added to dry HQDA-CPG (2) (1 g) in a separate polypropylene tube. The tube was capped and mixed on an inverting rotator for 20 hours at room temperature. The slurry was transferred to a syringe equipped with a frit and stopcock. The syringe was mounted on a vacuum manifold and the reaction flow and acetonitrile wash (2×10 mL) were collected for subsequent recovery of uncoupled nucleoside. The solid support was washed on the manifold with methanol (2×10 mL), acetonitrile (2×10 mL) methylene chloride (2×10 mL) and dried with vacuum.

The syringe was fitted with a closed stopcock and exposed to a solution of 16% 1-methylimidazole in THF (Pac$_2$O Cap B, 5 mL) followed by a solution of 5% (w/v) phenoxyacetic anhydride: 10% pyridine in THF (Pac$_2$O Cap A, 5 mL) was added to the dry CPG. The syringe barrel was plugged with a plunger and mixed on an inverting rotator for 30 minutes. The syringe was mounted on a vacuum manifold and washed with acetonitrile (3×10 mL), methylene chloride (2×10 mL) and dried with vacuum. The solid support was deblocked by flowing 3% dichloroacetic acid in methylene chloride (8×10 mL). The solid support was washed with acetonitrile until colorless and then washed with acetonitrile (3×10 mL) and methylene chloride (2×10 mL). After the washes, the solid support was dried on the vacuum manifold to provide (4).

Example 3

5'-Iodo-5-(Octa-1,7-diynyl)-2',5'-dideoxyuridine-3'-O-HQDA-CPG (5)

Iodination of compound (4) was performed according to the method of Miller and Kool, "A Simple Method for Electrophilic Functionalization of DNA," Org. Lett., 4(21), 3599-3601(2002). Solid support bound 5-(octa-1,7-diynyl)-2'-deoxyuridine-3'-O-HQDA-CPG (4) (330 mg) was transferred to a syringe fitted with a stopcock and loaded onto a vacuum manifold. The solid support was wetted with DMF (1×10 mL). Freshly prepared 0.5 M methyltriphenoxyphosphonium iodide in DMF (10 mL) was added to the syringe, the barrel was capped and the contents were mixed on an inverting rotator for 1 hour. The syringe was fitted on a vacuum manifold and washed with DMF (4×10 mL), acetonitrile (3×10 mL) and methylene chloride (3×10 mL). The solid support was dried with via vacuum to provide purified (5).

Example 4

5'-Azido-5-(Octa-1,7-diynyl)-2',5'-dideoxyuridine-3'-O-HQDA-CPG (6)

Sodium azide (130 mg, 20 mmol) and sodium iodide (300 mg, 20 mmol) were dissolved in DMF (20 mL) in an amber glass vial. A molecular sieve packet was added to the solution and let stand overnight. The next day, the 100 mmol azide/iodide solution (10 mL) was added to solid support bound 5'-iodo-5-(octa-1,7-diynyl)-2',5'-dideoxyuridine-3'-O-HQDA-CPG (5) (330 mg) in a 15 mL polypropylene tube. The solution was incubated at 50° C. for 3 hours with no agitation. The solid support was rinsed with DMF, centrifuged, and the DMF supernatant was decanted. The solid support was slurried with fresh DMF and transferred to a fritted syringe. The solid support was washed with DMF (3×10 mL), acetonitrile (3×10 mL) and methylene chloride (2×10 mL). The solid support was dried to a free flowing powder (6) on the vacuum manifold. See, e.g., Miller and Kool, "Versatile 5'-Functionalization on Solid Support: Amines, Azides, Thiols and Thioethers via Phosphorus Chemistry," J. Organic Chemistry, 69(7), 2404-2410 (2004).

A MS sample was prepared by transferring a small amount of (6) to a 2 mL screw cap tube. Cold NH$_4$OH (500 µL) was added to the solid support and then incubated at room temperature for 5 minutes. The CPG/NH$_4$OH slurry was transferred to a 3 mL syringe fitted with a 13 mm syringe filter with a 0.45 µm GHP Acrodisc filter (Pall Corporation, Ft. Washington, N.Y.). The plunger was fitted into the syringe barrel and the filtrate was collected into a 1.5 ml polypropylene tube. The CPG/Acrodisc were washed with cold NH$_4$OH (500 µL) followed by H$_2$O (500 µL) and added to the original filtrate. This solution was evaporated in a Savant Speedvac at 65° C. for 1 hour followed by evaporation at room temperature to reduce the volume to at least 150 µL. The crude material HPLC purified with a Cadenza CD-C18 column (4.6 mm×150 mm 3 µM) on the Prostar System using a gradient of 5% B to 39.5% B in 46 minutes at 1 mL/min and monitoring at 292 nm. The peak containing the 5'-azide (6) was sent to Numega Resonance Labs (San Diego, Calif.) for ESI MS analysis. The found m/z was in agreement with the calculated m/z for the structure shown below.

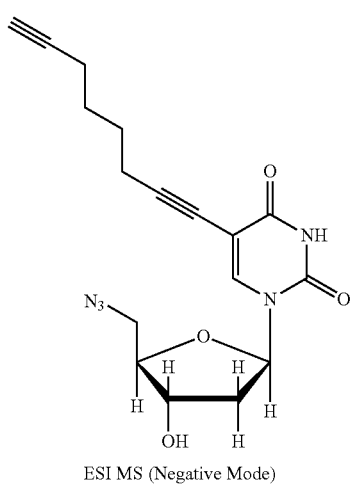

ESI MS (Negative Mode)

Calculated: 357. 37 amu
Found: 356 amu (M-H)

Example 5

5-Hexyn-1-yl-(2-Cyanoethyl)-methyl-Phosphite (7)

Phosphite (7) was prepared by dissolving 5-hexyn-1-yl-(2-cyanoethyl)-(N,N-diisopropyl)-phosphoramidite (403 µmole) in dry acetonitrile (4 mL) with 0.28 M 5-ethylthio-1H-tetrazole (1.726 mL, 84 mmol). Methanol (28 µL, 119 mmol) was added and sharp needles of N,N-diisopropylammonium ethylthiotetrazolide formed immediately. The solution was incubated at room temperature for 2 hours. The solution was separated from the crystals and the supernatant was divided into 4 polypropylene tubes and evaporated to form a solid mass (7).

Example 6

5'-N-(2-Cyanoethyl)-(5-Hexyn-1-yl)-Phosphoramidate-5-(Octa-1,7-diynyl)-2',5'-dideoxyuridine-3'-O-HQDA-CPG (8)

Solid support bound 5'-azido-5-(octa-1,7-diynyl)-2',5'-dideoxyuridine-3'-O-HQDA-CPG (6) (2.4 µmols/mg, 125 mg) was transferred to a fritted syringe and mounted on a vacuum manifold. The support was washed with acetonitrile (3×1 ml). The support was dried in vacuo and transferred to a polypropylene tube. To the tube was added 0.7M solution of 5-hexyn-1-yl-(2-cyanoethyl)-methyl-phosphite (7) in DMSO (429 µL, 300 µmol) and a 2.5 M solution of LiCl in DMSO (300 µL, 750 umol). The tube was capped and placed on a heated mixer and set to 55° C. and 400 rpm for 24 hours followed by mixing at room temperature for 12 hours. The tube was centrifuged to pellet the solid support. The solid support was transferred to a fritted syringe, mounted on a vacuum manifold and washed with DMF (3×1 mL), acetonitrile (2×1 mL), H$_2$O (1×1 mL) and acetonitrile (3×1 mL). The solid (8) was dried by vacuum on the manifold.

A MS sample was prepared by transferring a small amount of (8) to a 2 mL screw cap tube. Cold NH$_4$OH (500 µL) was added to the solid support and then incubated at room temperature for 5 minutes. The CPG/NH$_4$OH slurry was transferred to a 3 mL syringe fitted with a 13 mm syringe filter with a 0.45 µm GHP Acrodisc filter (Pall Corporation, Ft. Washington, N.Y.). The plunger was fitted into the syringe barrel and the filtrate was collected into a 1.5 ml polypropylene tube. The CPG/Acrodisc were washed with cold NH$_4$OH (500 µL) followed by H$_2$O (500 µL) and added to the original filtrate. This solution was evaporated in a Savant Speedvac at 65° C. for 1 hour followed by evaporation at room temperature to reduce the volume to at least 150 µL. The crude material HPLC purified with a Cadenza CD-C18 column (4.6 mm×150 mm 3 µM) on the Prostar System using a gradient of 5% B to 39.5% B in 46 minutes at 1 mL/min and monitoring at 292 nm. The peak containing the (8) was sent to Numega Resonance Labs (San Diego, Calif.) for ESI MS analysis. The found m/z was in agreement with the calculated m/z for the structure shown below.

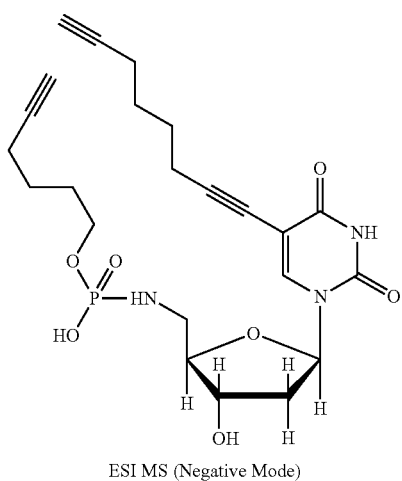

ESI MS (Negative Mode)

Calculated: 491.48 amu
Found: 490 amu (M-H)

Example 7

Protected 5'-Triphosphoramidate P$_\alpha$-(5-Hexyn-1-yl)-5-(octa-1,7-diynyl)-2',5'-dideoxyuridine-3'-O-HQDA-CPG (10)

The diphosphate (9) and triphosphate (10) were prepared from 5'-N-(2-Cyanoethyl)-(5-hexyn-1-yl)-phosphoramidate-5-(octa-1,7-diynyl)-2',5'-dideoxyuridine-3'-O-HQDA-CPG (8) (125 mg) on solid support using a MerMade 12 synthesizer. The synthesis was performed with the following 2 basic automated steps: (R) Removal of the cyanoethyl phosphate protecting group; (C) Coupling of the Bis-CNET and oxidation to P(V) phosphate. The sequence of additions and delivery volumes for these routines are set forth below:

Removal of cyanoethyl protecting group (R) was performed as summarized in Table 1.

TABLE 1

| # Additions | Reagent | Step | uL per Addition | Total uL |
|---|---|---|---|---|
| 3 | 10% DBU/45% BSA in ACN | Deprotection | 250 | 750 |
| 1 | — | Drain | — | — |
| 3 | 10% DBU/45% BSA in ACN | Deprotection | 250 | 750 |
| 1 | — | Drain | — | — |
| 3 | 10% DBU/45% BSA in ACN | Deprotection | 250 | 750 |
| 2 | — | Drain | — | — |
| 6 | ACN | Wash | 300 | 1800 |
| 1 | — | Drain | — | — |
| 4 | DCM | Wash | 250 | 1000 |
| 3 | — | Drain | — | — |

Coupling of Bis-CNET and oxidation to P(V) phosphate (C) was done as summarized in Table 2.

TABLE 2

| # Additions | Reagent | Step | uL per Addition | Total uL |
|---|---|---|---|---|
| 3 | Bis-CNEt PPA | Coupling | 95 | 285 |
|  | ETT | Activator | 110 | 330 |
| 1 | ACN | Wash | 300 | 300 |
| 1 | — | Drain | — | — |
| 3 | 1.1M t-BuOOH | Oxidation | 200 | 600 |
| 1 | — | Drain | — | — |
| 3 | DCM | Wash | 250 | 750 |
| 1 | — | Drain | — | — |
| 3 | ACN | Wash | 300 | 900 |
| 2 | — | Drain | — | — |

The order of the automated steps used to make the triphosphoramidate are summarized in Table 3.

TABLE 3

| Command | Treatment |
|---|---|
| R | Remove α phosphate cnet |
| C | Couple and oxidize β phosphate |
| R | Remove β phosphate cnet |
| C | Couple and oxidize γ phosphate |
| R | Remove γ phosphate cnet |

Example 8

5'-Triphosphoramidate P$_\alpha$-(5-Hexyn-1-yl)-5-(octa-1,7-diynyl)-2',5'-dideoxyuridine (11)

Solid support bound 5'-triphosphoramidate Pa-(5-hexyn-1-yl)-5-(octa-1,7-diynyl)-2',5'-dideoxyuridine-3'-O-HQDA-CPG (10) (125 mg) was weighed into a 2 mL polypropylene tube. Cold NH$_4$OH (500 µL) was added to the solid support and then incubated at room temperature for 5 minutes. The CPG/NH$_4$OH slurry was transferred to a 3 mL syringe fitted with a 13 mm syringe filter with a 0.45 µm GHP Acrodisc filter (Pall Corporation, Ft. Washington, N.Y.). The plunger was fitted into the syringe barrel and the filtrate was collected into a 1.5 ml polypropylene tube. The CPG/Acrodisc were washed with cold NH$_4$OH (500 µL) followed by H$_2$O (500 µL) and added to the original filtrate. This solution was evaporated in a Savant Speedvac at 65° C. for 1 hour followed by evaporation at room temperature to reduce the volume to at least 150 µL. The crude material (11) was quantified by UV.

HPLC purification was performed on a Cadenza CD-C18 column (4.6 mm×150 mm 3 µM) on the Prostar System using a gradient of 5% B to 39.5% B in 46 minutes at 1 mL/min and monitoring at 292 nm. The peak containing the triphosphoramidate (11) was sent to Numega Resonance Labs (San Diego, Calif.) for ESI MS analysis. Calculated m/z: 651.44 amu. Found: 650 amu (M-H).

In Example 2, 5'-O-dimethoxytriyl-5-(octa-1,7-diynyl)-2'-deoxyuridine (3) was employed as a starting material, so that the subsequently formed compounds 4-11 each contained the uracil nucleobase. This same synthetic route may be employed with suitable alternative octadiynyl 2'-deoxynucleosides to (3) so as to incorporate alternative nucleobases into a compound of Formula 1 as disclosed herein. For example, N$^6$-protected 5'-DMT-2'-deoxy-7-octadiynyl-7-deazaadenosine, N$^4$-protected-5-octadiynyl-5'-DMT-2'-deoxycytidine, and N2-protected-5'-DMT-2'-deoxy-7-octadiynyl-7-deazaguanosine may be used in lieu of the 5-octadiynyl-5'-DMT-2'-deoxyuridine (3).

Synthetic Scheme B provides an outline of a methodology according to the present disclosure which is described in more detail in numbered Examples 9-12. The compounds 6 and 11-16 from Scheme B were used and/or synthesized in a glove box in a positive pressure argon atmosphere.
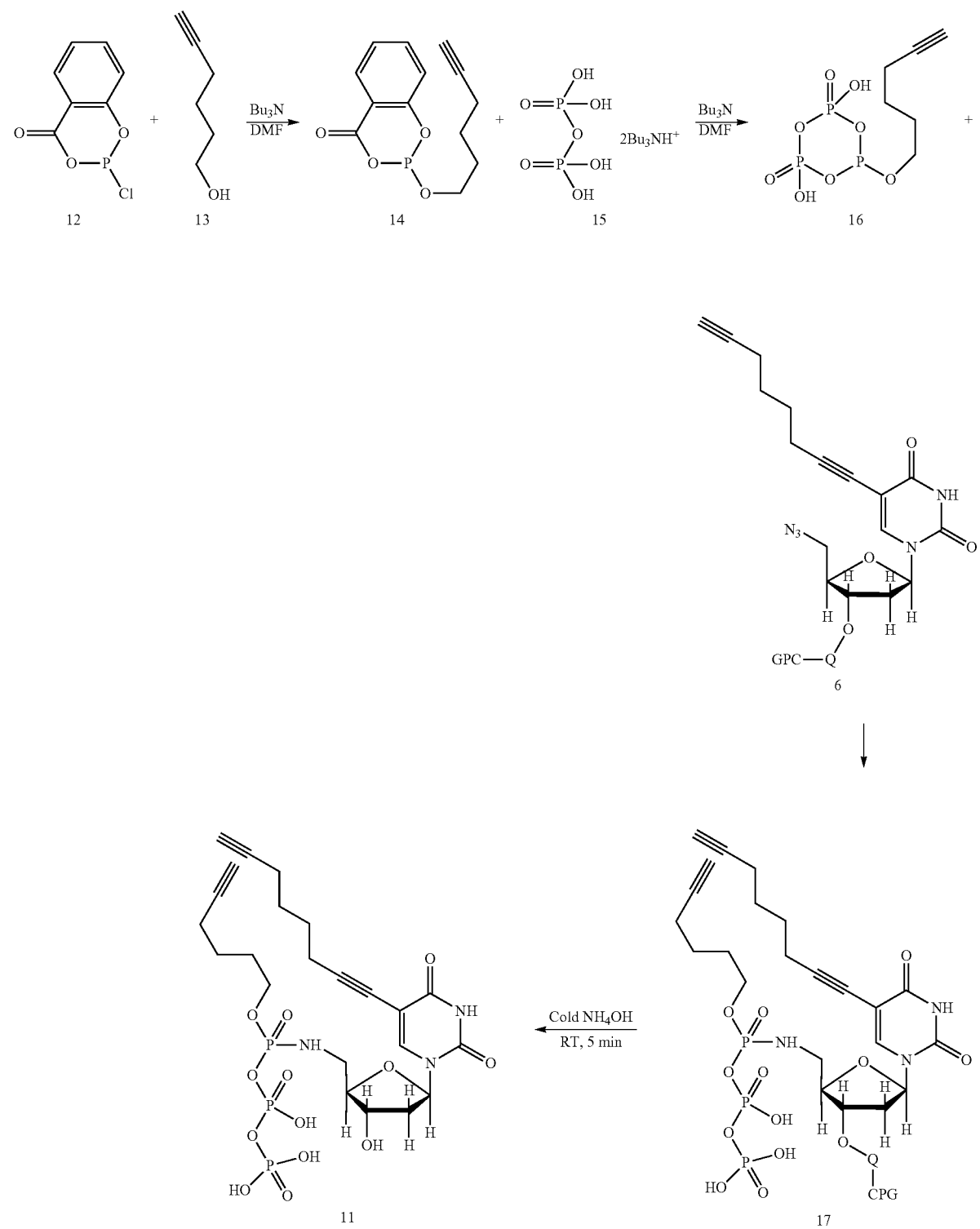

Example 9

Salicyl-(5-Hexyn-1-yl)-phosphite (14)

In a polypropylene tube, 5-hexyn-1-ol (13) (25 µL, 220 µmol) was added to tributylamine (95 µL, 400 µmol) in DMF (343 µL). In a separate polypropylene tube, 2-chloro-4H-1,3,2-benzodioxaphosphorin-4-one (12) (81 mg, 400 µmol) was dissolved in DMF (200 µL). See, e.g., Ludwig and Eckstein, "Synthesis of Nucleoside 5'-O-(1,3-Dithiotriphosphates) and 5'-O-(1,1-Dithiotriphosphates)", J. Org. Chem, 56, 1777-1783 (1991). The two DMF solutions were mixed and incubated at room temperature for 30 minutes to provide salicyl-(5-hexyn-1-yl)-phosphite (14), which was used directly in the process described in Example 10.

Example 10

$P^1$-(5-Hexyn-1-yl)-$P^2$,$P^3$-dioxo-cyclotriphosphite (16)

Salicyl-(5-hexyn-1-yl)-phosphite (14) solution from Example 9 was added to a mixture of tributylamine (95 µmol, 400 µmol) in 0.5M bis-tributylammonium pyrophosphate (15) in DMF (440 µL, 220 µmol) and the solution was incubated at room temperature for 90 minutes to provide the cyclic triphosphite (16). See, e.g., Ludwig and Eckstein, "Synthesis of Nucleoside 5'-O-(1,3-Dithiotriphosphates) and 5'-O-(1,1-Dithiotriphosphates)", J. Org. Chem, 56, 1777-1783 (1991). The resulting solution was used in Example 11.

Example 11

5'-Triphosphoramidate $P_\alpha$-(5-Hexyn-1-yl)-5-(octa-1,7-diynyl)-2',5'-dideoxyuridine-3'-O-HQDA-CPG (17)

5'-Azido-5-(octa-1,7-diynyl)-2',5'-dideoxyuridine-3'-O-HQDA-CPG (6) (9 mg) was mixed with the solution containing compound 16 from Example 10, and the slurry was incubated at room temperature for 24 hours to provide 5'-triphosphoramidate Pa-(5-hexyn-1-yl)-5-(octa-1,7-diynyl)-2',5'-dideoxyuridine-3'-O-HQDA-CPG (17). The slurry was transferred to a fritted Luer tip column (Bioautomation, Plano, Tex.) and fitted onto a vacuum manifold. The reaction solution was drained and the CPG-bound derivative (17) was washed with DMF (1×500 µL) followed by more DMF (2×1 mL) and then ACN (2×1 mL). The CPG derivative (17) was dried by vacuum on the manifold.

Example 12

5'-Triphosphoramidate $P_\alpha$-(5-Hexyn-1-yl)-5-(octa-1,7-diynyl)-2',5'-dideoxyuridine (11)

Solid support bound 5'-triphosphoramidate Pa-(5-hexyn-1-yl)-5-(octa-1,7-diynyl)-2',5'-dideoxyuridine-3'-O-HQDA-CPG (17) was deprotected and released from the solid support according to the method of Example 8 with cold $NH_4OH$ to provide 5'-triphosphoramidate Pa-(5-hexyn-1-yl)-5-(octa-1,7-diynyl)-2',5'-dideoxyuridine (11).

The skilled person may refer to one or more of the following documents for additional information regarding the identification and synthetic methods that may be applied to the preparation of the compounds and precursors thereof, of the present disclosure. Synthesis of phosphoromonoamidate diesters (Staudinger Reaction followed by Michaelis-Arbuzov Reaction) is discussed in, e.g., Letsinger and Heavner, "Synthesis of Phosphoromonoamidate Diester Nucleotides via the Phosphite-Azide Coupling Method," Tetrahedron Letters, 16(2), 147-150 (1975). The identification and synthesis of LNA nucleosides is discussed in, e.g., Wengel et al., "LNA (Locked Nucleic Acids): Synthesis of the adenine, cytosine, guanine, 5-methylcytosine, thymine, and bicyclonucleoside monomers, oligomerisation, and unprecedented nucleic acid recognition," Tetrahedron, 54(12), 3607-3630 (1998). Identification and synthesis of acyclic nucleosides is discussed in, e.g., Wengel et al., "UNA (unlocked nucleic acid): A flexible RNA mimic that allows engineering of nucleic acid duplex stability," Bioorganic & Medicinal Chemistry, 17(15), 5420-5425 (2009). The identification and use of phosphate and other protecting groups is discussed in, e.g., Peter G. M. Wuts, "Greene's Protective Groups in Organic Synthesis: Fifth Edition, Wiley, 2014.

Although any methods and materials similar or equivalent to those described herein can also be used in the practice of the present invention, a limited number of the exemplary methods and materials have been illustrated in detail.

The present disclosure provides the following numbered embodiments, which are exemplary only of the embodiments of the present invention:

1) A compound of the formula

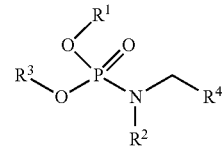

wherein
$R^1$ is selected from
  a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and
  b) an alkyl group and an oxyalkyl group, either of which terminates in a linker group (LG1), the LG1 bonded to a tether (T);
$R^2$ is selected from hydrogen and $C_1$-$C_4$alkyl;
$R^3$ is selected from $R^5$ and —[Pn-O]$_m$—$R^5$, where Pn is independently selected from P(OR$^5$) and P(=O)(OR$^5$) at each occurrence, and m is selected from 1, 2, 3, 4, 5 and 6;
$R^4$ is selected from

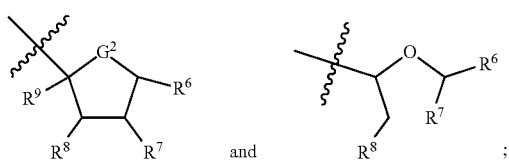

$R^5$ is selected from H and $G^1$;
$R^6$ is a heterocycle, the heterocycle optionally comprising a substituent $R^{13}$, where $R^{13}$ is selected from
  a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and b) an alkyl group and an oxyalkyl group, either of which terminates in a linker group (LG2), the LG2 bonded to the tether (T);

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker;

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and $CH_2$; and $G^3$ is a protecting group for a hydroxyl group that is bonded to a carbon atom.

2) The compound of embodiment 1 wherein each of $R^1$ and $R^{13}$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen.

3) The compound of embodiment 2 wherein $R^1$ is —$(CH_2)_q$—C≡CH, $R^{13}$ is —C≡C—$(CH_2)_q$—C≡CH and q is an integer selected from 2-10.

4) The compound of embodiment 1 wherein each of $R^1$ and $R^{13}$ is selected from an alkyl group and an oxyalkyl group, either of which terminates in a linker group (LG1), the LG1 bonded to a tether (T).

5) The compound of embodiment 4 wherein LG1 and LG2 are triazole groups.

6) The compound of each of embodiments 1, 2, 3, 4 and 5 wherein $R^3$ is selected from

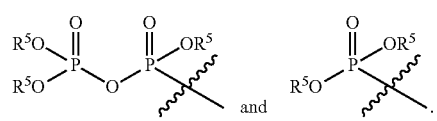

7) The compound of each of embodiments 1, 2, 3, 4, 5 and 6 wherein $R^4$ is

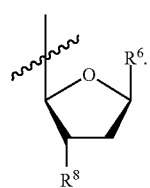

8) The compound of embodiment 1 wherein $R^6$ is selected from:

an adenosine analog of formula

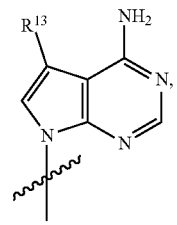

a guanosine analog of formula

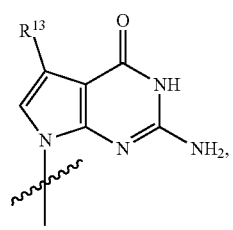

a uridine analog of formula and

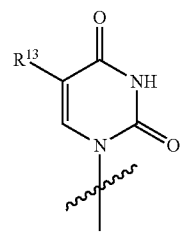

a cytidine analog of formula

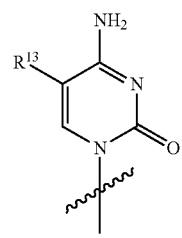

and wherein $R^{13}$ is selected from a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and b) an alkyl group and an oxyalkyl group, either of which terminates in a linker group (LG2), the LG2 bonded to the tether (T).

9) The compound of embodiment 1 having the formula

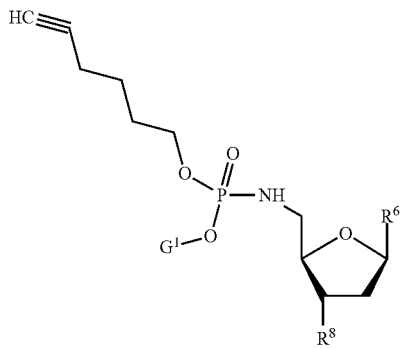

wherein:

$G^1$ is H or a protecting group;

$R^6$ is a heterocycle comprising a substituent $R^{13}$;

$R^8$ is selected from $OR^{11}$ and O-L-SS where SS represents a solid support and L represents a linking group between O and the SS;

$R^{11}$ is selected from H and $G^3$; and $G^3$ is a protecting group for a hydroxyl group that is bonded to a carbon atom.

10) The compound of embodiment 1 having the formula

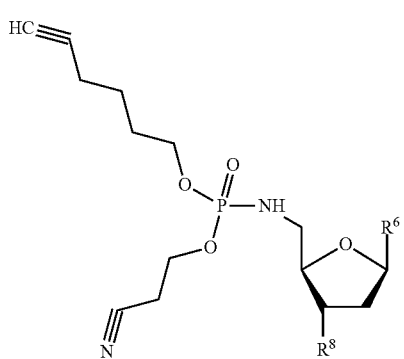

wherein:

$R^6$ is a heterocycle comprising a substituent $R^{13}$;

$R^8$ is —$OR^{11}$ or —O-L-SS where L-SS represents a solid support bound to a linker;

$R^{11}$ is selected from H and $G^3$; and $G^3$ is a protecting group for a hydroxyl group that is bonded to a carbon atom.

11) The compound of embodiment 1 having a formula selected from the group

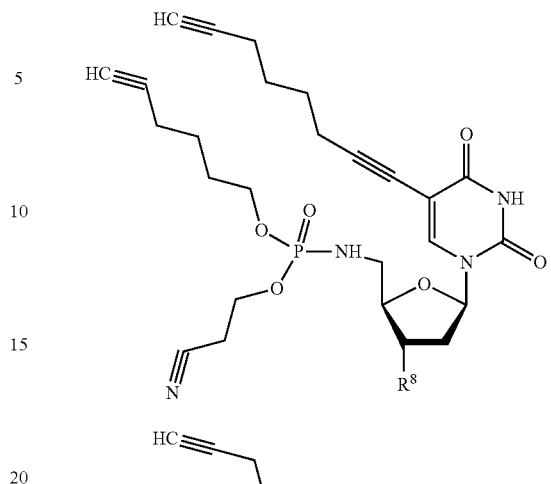

(4c)

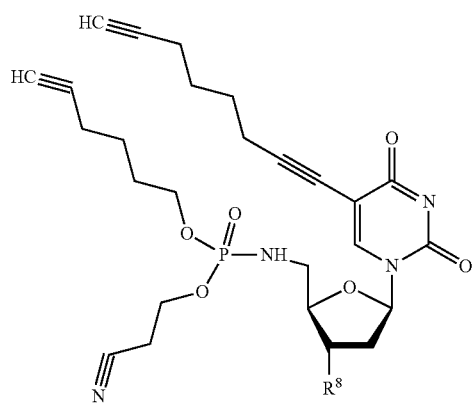

(4d)

(4e)

, and

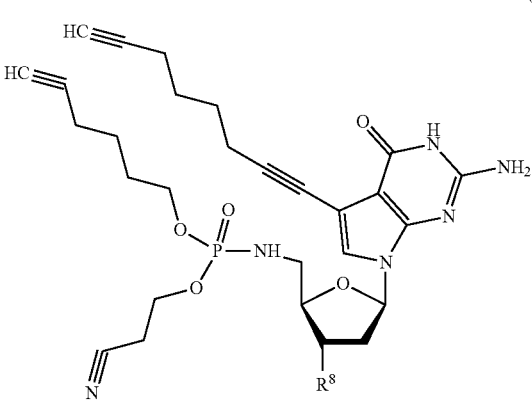

(4f)

wherein:

$R^8$ is —$OR^{11}$ or —O-L-SS where L-SS represents a solid support bound to a linker;

$R^{11}$ is selected from H and $G^3$; and $G^3$ is a protecting group for a hydroxyl group that is bonded to a carbon atom.

12) The compound of embodiment 1 wherein each of LG1 and LG2 is a triazole group.

13) A process of forming a phosphoromonoamidate diester 110 from a phosphite triester compound (100) and an azide compound (105),

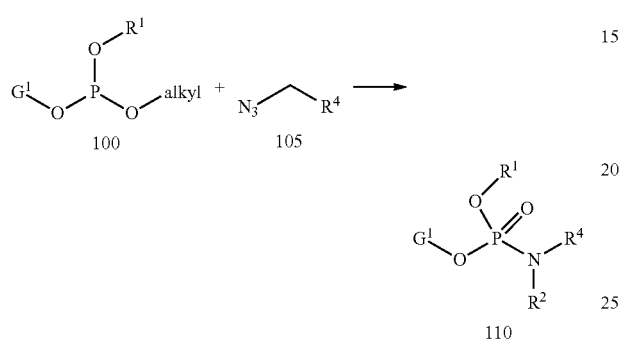

the process comprising combining (100) with (105) in the presence of a halide anion, wherein:

$R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^2$ is selected from hydrogen and $C_1$-$C_4$alkyl;

$R^4$ is selected from

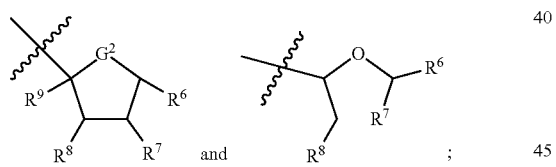

$R^6$ is a heterocycle, the heterocycle optionally comprising a substituent $R^{13}$, where $R^{13}$ is selected from
  a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and
  b) an alkyl group and an oxyalkyl group, either of which terminates in a linker group (LG2), the LG2 bonded to the tether (T);

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support bound to a linker (L);

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

$G^2$ is selected from oxygen, sulfur and $CH_2$; and $G^3$ is a protecting group for a hydroxyl group that is bonded to a carbon atom.

14) A process for forming a phosphate protected N-phosphoroamidate-monoester disphosphate (120) from a phosphoramidate diester compound (110) and a phosphorylating phosphoramidite compound 115,

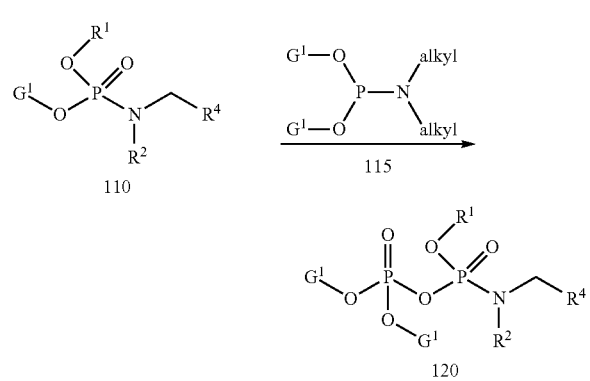

the process comprising combining (110) with a base and a silylating agent to provide a first intermediate, combining the first intermediate with (115) and an activator to provide a second intermediate, and combining the second intermediate with an oxidizing agent to form the phosphate protected N-phosphoroamidate-monoester diiphosphate (120), wherein:

$R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

$R^2$ is selected from hydrogen and $C_1$-$C_4$alkyl;

$R^4$ is selected from

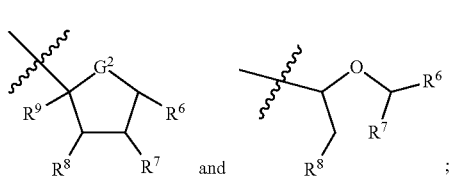

$R^6$ is a heterocycle, the heterocycle optionally comprising a substituent $R^{13}$, where $R^{13}$ is selected from
  a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and
  b) an alkyl group and an oxyalkyl group, either of which terminates in a linker group (LG2), the LG2 bonded to the tether (T);

$R^7$ is selected from hydrogen, —$CH_2$-halogen, $C_1$-$C_4$alkyl, hydroxyl and —$CH_2$—$OR^{10}$;

$R^8$ is —$OR^{11}$ or —O-L-SS where L-SS represents a solid support optionally bound to a linker (L);

$R^9$ is hydrogen or, when $R^7$ is —$CH_2$—$OR^{10}$ then $R^9$ may be —$CH_2$—$R^{12}$ where $R^{10}$ and $R^{12}$ form a direct bond;

$R^{11}$ is selected from H and $G^3$;

$G^1$ is H or a protecting group for a hydroxyl group that is bonded to a phosphorous atom;

65

G² is selected from oxygen, sulfur and CH₂; and
G³ is a protecting group for a hydroxyl group that is bonded to a carbon atom.

15) A process for forming a phosphate protected N-phosphoroamidate-monoester triphosphate (125) from a phosphate protected N-phosphoroamidate-monoester diphosphate compound (120) and a phosphorylating phosphoramidite compound (115),

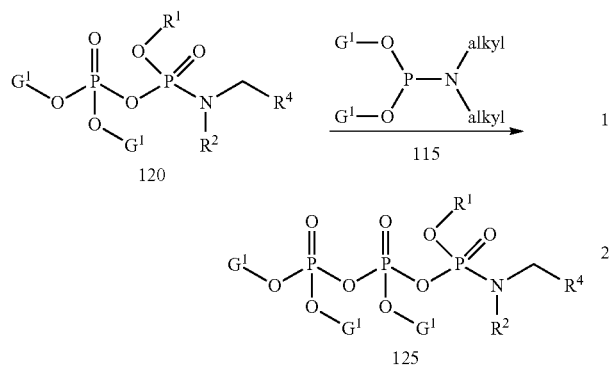

the process comprising combining (120) with a base and a silylating agent to provide a first intermediate, combining the first intermediate with (115) and an activator to provide a second intermediate, and combining the second intermediate with an oxidizing agent to form the phosphate protected N-phosphoroamidate-monoester triphosphate (125), wherein:

R¹ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

R² is selected from hydrogen and C₁-C₄alkyl;

R⁴ is selected from

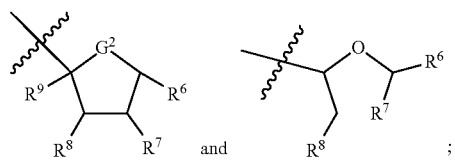

R⁶ is a heterocycle, the heterocycle optionally comprising a substituent R¹³, where R¹³ is selected from
 a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and
 b) an alkyl group and an oxyalkyl group, either of which terminates in a linker group (LG2), the LG2 bonded to the tether (T);

R⁷ is selected from hydrogen, —CH₂-halogen, C₁-C₄alkyl, hydroxyl and —CH₂—OR¹⁰;

R⁸ is —OR¹¹ or —O-L-SS where L-SS represents a solid support optionally bound to a linker;

R⁹ is hydrogen or, when R⁷ is —CH₂—OR¹⁰ then R⁹ may be —CH₂—R¹² where R¹⁰ and R¹² form a direct bond;

R¹¹ is selected from H and G³;

66

G¹ is H or a protecting group for a hydroxyl group that is bonded to a phosphorous atom;
G² is selected from oxygen, sulfur and CH₂; and
G³ is a protecting group for a hydroxyl group that is bonded to a carbon atom.

16) A process for forming a N-phosphoroamidate-monoester triphosphate (160) from a cyclotriphosphite (155) and an azide (105)

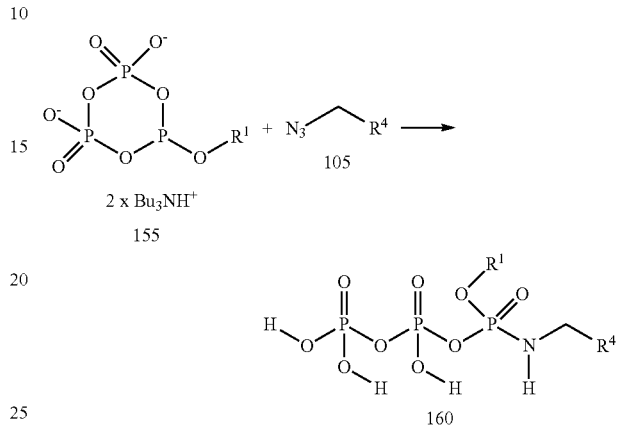

the process comprising combining (155) and (105) in the presence of solvent so as to form (160), wherein:

R¹ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen;

R⁴ is selected from

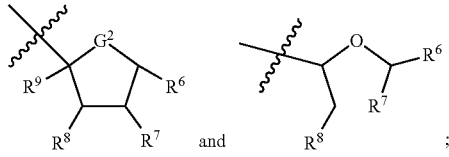

R⁶ is a heterocycle, the heterocycle optionally comprising a substituent R¹³, where R¹³ is selected from
 a) an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen; and
 b) an alkyl group and an oxyalkyl group, either of which terminates in a linker group (LG2), the LG2 bonded to the tether (T);

R⁷ is selected from hydrogen, —CH₂-halogen, C₁-C₄alkyl, hydroxyl and —CH₂—OR¹⁰;

R⁸ is —OR¹¹ or —O-L-SS where L-SS represents a solid support optionally bound to a linker;

R⁹ is hydrogen or, when R⁷ is —CH₂—OR¹⁰ then R⁹ may be —CH₂—R¹² where R¹⁰ and R¹² form a direct bond;

R¹¹ is selected from H and G³;

G² is selected from oxygen, sulfur and CH₂; and
G³ is a protecting group for a hydroxyl group that is bonded to a carbon atom.

17) The process of embodiment 16 further comprising reacting the N-phosphoroamidate-monoester triphosphate (160) with a tether precursor of the formula X-T-X where X represents a reactive functional group that is reactive with the terminating functional group of $R^1$ and $R^{13}$, so as to form linker groups LG1 and LG2.

18) The process of embodiment 17 wherein X is an azide group and the terminating functional groups of $R^1$ and $R^{13}$ are alkyne groups.

19) A cyclic phosphite of the formula

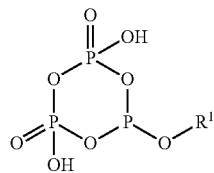

wherein $R^1$ is selected from an alkyl group and an oxyalkyl group, either of which terminates in a functional group selected from carbon-carbon double bond, carbon-carbon triple bond, hydroxyl, amine, azide, hydrazine, thiol, carboxyl, formyl, hydroxylamino and halogen.

20) The cyclic phosphite of embodiment 20 wherein $R^1$ is a terminally functionalized alkyl group, where the functional group is a carbon-carbon triple bond.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, including but not limited to U.S. Pat. Nos. 8,586,301 and 8,592,182 as well as US Patent Publication Nos. 2014/134618 (now issued as U.S. Pat. No. 9,670,526) and 2015/0284787, (now issued as U.S. Pat. No. 9,771,614), are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

However, all structures encompassed within a claim are "chemically feasible", by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds.

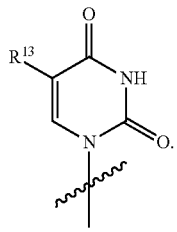

10. The compound of claim 1 wherein $R^6$ is an a 1-cytosinyl analog of formula
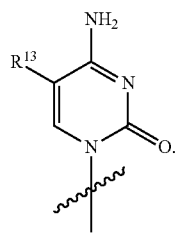

What is claimed is:

1. A compound of the formula:

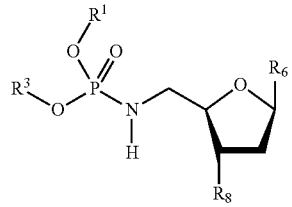

wherein

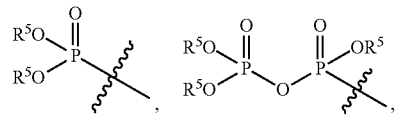

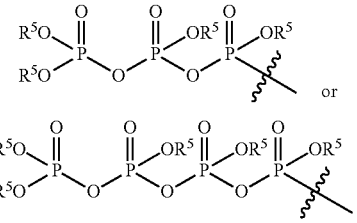

$R^5$ is H;

$R^6$ is:

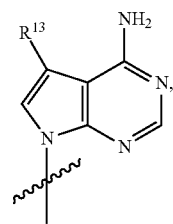

7-deaza-9-adeninyl analog of formula

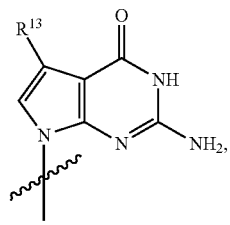

7-deaza-9-guaninyl analog of formula

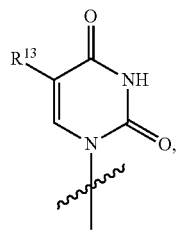

a 1-uracilyl analog of formula or

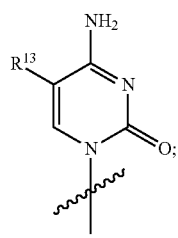

a 1-cytosinyl analog of formula
$R^8$ is —$OR^{11}$;
$R^{11}$ is H; and
$R^1$ and $R^{13}$ are taken together to form a tether segment which allows for linear expansion of the compound upon cleavage of the phosphoramidate bond, wherein the tether is a polymer or a molecular construct having two opposing ends and a generally linear dimension, the ends being attached at the $R^1$ and $R^{13}$ positions by a linkage comprising a triazole group, and wherein the tether segment comprises a reporter construct,
and wherein the compound prior to cleavage of the phosphoramidate bond is in a constrained configuration and upon cleavage of the phosphoramidate bond is in an expanded configuration, such that cleavage of the phosphoramidate bond provides for controlled linear expansion of the compound.

2. The compound of claim 1 wherein $R^3$ is $R^5$.
3. The compound of claim 1 wherein $R^3$ is

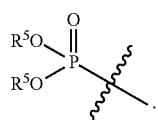

4. The compound of claim 1 wherein $R^3$ is

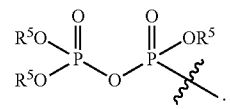

5. The compound of claim 1 wherein $R^3$ is

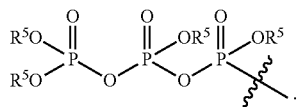

6. The compound of claim 1 wherein $R^3$ is

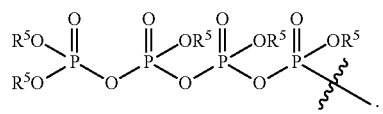

7. The compound of claim 1 wherein $R^6$ is a 7-deaza-9-adeninyl analog of formula

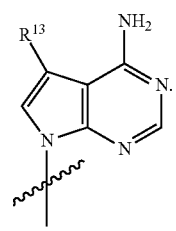

8. The compound of claim 1 wherein $R^6$ is an a 7-deaza-9-guaninyl analog of formula

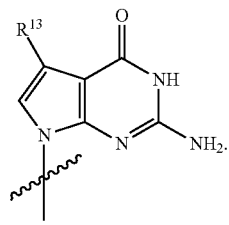

9. The compound of claim 1 wherein $R^6$ is an a 1-uracilyl analog of formula